US011065217B2

(12) United States Patent
Spector et al.

(10) Patent No.: US 11,065,217 B2
(45) Date of Patent: Jul. 20, 2021

(54) USE OF SHORT CHAIN FATTY ACIDS FOR THE TREATMENT AND PREVENTION OF DISEASES AND DISORDERS

(71) Applicant: Temple University—Of The Commonwealth System of Higher Education, Philadelphia, PA (US)

(72) Inventors: Ira C. Spector, Jenkintown, PA (US); Mark A. Feitelson, North Wales, PA (US); Alla Arzumanyan, Huntingdon Valley, PA (US)

(73) Assignee: TEMPLE UNIVERSITY—OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 0 days.

(21) Appl. No.: 15/903,514

(22) Filed: Feb. 23, 2018

(65) Prior Publication Data
US 2018/0214399 A1   Aug. 2, 2018

Related U.S. Application Data

(63) Continuation of application No. PCT/US2018/015383, filed on Jan. 26, 2018.

(60) Provisional application No. 62/451,192, filed on Jan. 27, 2017, provisional application No. 62/510,867, filed on May 25, 2017, provisional application No. 62/510,872, filed on May 25, 2017, provisional application No. 62/530,371, filed on Jul. 10, 2017, provisional application No. 62/539,572, filed on Aug. 1, 2017, provisional application No. 62/588,961, filed on Nov. 21, 2017.

(51) Int. Cl.
| | | |
|---|---|---|
| A61K 31/19 | (2006.01) | |
| A61K 9/48 | (2006.01) | |
| A61K 9/00 | (2006.01) | |
| A61K 45/06 | (2006.01) | |
| A61P 37/08 | (2006.01) | |
| A61P 27/02 | (2006.01) | |
| A61P 35/00 | (2006.01) | |
| A61P 17/00 | (2006.01) | |

(52) U.S. Cl.
CPC ............ *A61K 31/19* (2013.01); *A61K 9/0014* (2013.01); *A61K 9/0048* (2013.01); *A61K 9/4891* (2013.01); *A61K 45/06* (2013.01); *A61P 17/00* (2018.01); *A61P 27/02* (2018.01); *A61P 35/00* (2018.01); *A61P 37/08* (2018.01); *A61K 2300/00* (2013.01)

(58) Field of Classification Search
CPC .... A61K 31/19; A61K 9/0014; A61K 9/0048; A61K 9/4891; A61K 45/06; A61P 27/02; A61P 17/00; A61P 37/08; A61P 35/00
See application file for complete search history.

(56) References Cited

U.S. PATENT DOCUMENTS

| | | | |
|---|---|---|---|
| 4,735,967 A * | 4/1988 | Neesby | A61K 31/19 514/557 |
| 5,919,822 A | 7/1999 | Cotter et al. | |
| 6,232,345 B1 | 5/2001 | Hiraide et al. | |
| 7,208,516 B2 | 4/2007 | Muller et al. | |
| 7,303,889 B2 | 12/2007 | LePoul et al. | |
| 7,399,787 B2 | 7/2008 | Chiao et al. | |
| 9,764,019 B2 | 9/2017 | Honda et al. | |
| 2002/0111495 A1 | 8/2002 | Magee et al. | |
| 2004/0018968 A1 | 1/2004 | Sgouros et al. | |
| 2004/0127523 A1 | 7/2004 | Bacopoulos et al. | |
| 2006/0258698 A1 | 11/2006 | Mudumba et al. | |
| 2007/0203173 A1 | 8/2007 | Mudumba et al. | |
| 2008/0003329 A1 | 1/2008 | Rueda et al. | |
| 2008/0004311 A1 | 1/2008 | Hellberg | |
| 2008/0107646 A1* | 5/2008 | Chung | A61K 31/19 424/131.1 |
| 2011/0300238 A1* | 12/2011 | Eritzland | A61P 17/08 424/692 |
| 2013/0115280 A1* | 5/2013 | Moro | A61K 9/2013 424/451 |
| 2013/0210763 A1 | 8/2013 | Speelmans et al. | |
| 2013/0323215 A1 | 12/2013 | Foo et al. | |
| 2014/0065114 A1 | 3/2014 | Lin et al. | |
| 2015/0056276 A1* | 2/2015 | Fraser | A23L 33/155 424/463 |
| 2016/0045475 A1* | 2/2016 | Day | A61K 39/3955 424/134.1 |

FOREIGN PATENT DOCUMENTS

| | | |
|---|---|---|
| EP | 0844001 A1 | 5/1998 |
| EP | 2033635 A1 | 3/2009 |
| WO | 1995011699 A1 | 5/1995 |
| WO | 2004024160 A1 | 3/2004 |
| WO | 2004112508 A1 | 12/2004 |
| WO | 2005023179 A2 | 3/2005 |
| WO | 2012013495 A1 | 2/2012 |
| WO | 2012131069 A1 | 10/2012 |
| WO | 2014033453 A1 | 3/2014 |
| WO | 2016118730 A1 | 7/2016 |
| WO | 2017021476 A1 | 2/2017 |
| WO | 2017042337 A1 | 3/2017 |
| WO | 2018/027274 A1 | 2/2018 |

OTHER PUBLICATIONS

Ala-Houhala et al. (Acta Derm Venereol, 2014, 94, 146-151).*

(Continued)

*Primary Examiner* — Genevieve S Alley
(74) *Attorney, Agent, or Firm* — Riverside Law LLP

(57) ABSTRACT

The invention relates to compositions and methods that include short chain fatty acids (SCFAs), related therapeutic compounds, and other compounds, including combinations thereof, for the treatment or prevention of diseases or disorders.

15 Claims, 6 Drawing Sheets

(56) References Cited

OTHER PUBLICATIONS

Lv et al., "The Antiepileptic Drug Valproic Acid Restores T Cell Homeostasis and Ameliorates Pathogenesis of Experimental Autoimmune Encephalomyelitis", The Journal of Biological Chemistry vol. 287, No. 34, pp. 28656-28665 (2012).
Mizuno et al., "The dual role of short fatty acid chains in the pathogenesis of autoimmune disease models", PLoS One, vol. 12(2): e0173032; pp. 1-15 (2017).
Nakamura et al., Short chain fatty acids ameliorate immune-mediated uveitis partially by altering migration of lymphocytes from the intestine, Sci Rep. (2017), vol. 7(1):11745: pp. 1-12.
Chen et al., Sodium butyrate regulates Th17/Treg cell balance to ameliorate uveitis via the Nrf2/HO-1 pathway. Biochem Pharmacol. vol. 142:111-119 (2017).
Bian et al., "Inhibition of NLRP3 Inflammasome Pathway by Butyrate Improves Corneal Wound Healing in Corneal Alkali Burn", Int J Mol Sci. 18(3):pp. 1-14 (2017).
Nakamura et al., "D-beta-hydroxybutyrate protects against corneal epithelial disorders in a rat dry eye model with logging board", Invest Ophthalmol Vis Sci. vol. 46(7):2379-87 (2005).
Nakamura et al., "Protective effect of D-beta-hydroxybutyrate on corneal epithelia in dry eye conditions through suppression of apoptosis", Invest Ophthalmol Vis Sci. 2003;44(11):4682-8.
Consolandi et al., "Behçet's syndrome patients exhibit specific microbiome signature", Autoimmun Rev. 2015; vol. 14(4):pp. 269-276.
Ogawa et al., "Sodium butyrate inhibits angiogenesis of human intestinal microvascular endothelial cells through COX-2 inhibition", FEBS Lett. 2003;554(1-2):88-94.
Ambati et al., "Mechanisms of age-related macular degeneration", Neuron, 2012; vol. 75(1):26-39.
Canani et al., "The epigenetic effects of butyrate: potential therapeutic implications for clinical practice", Clinical Epigenetics, 2012; vol. 4(4):pp. 1-7.
Yuan et al., "IL-6-induced survival of colorectal carcinoma cells is inhibited by butyrate through down-regulation of the IL-6 receptor", Carcinogenesis. 2004; vol. 25(11):2247-55.
Nastasi et al., "Butyrate and propionate inhibit antigen-specific CD8(+) T cell activation by suppressing IL-12 production by antigen-presenting cells", Sci Rep. 2017; vol. 7(1):14516:pp. 1-10.
Li et al., "Sodium butyrate exerts neuroprotective effects by restoring the blood-brain barrier in traumatic brain injury mice", Brain Res. 2016; vol. 1642:70-78.
Sivan et al., Hubert N. Commensal Bifidobacterium promotes antitumor immunity and facilitates anti-PD-L1 efficacy. Science. 2015; vol. 350:1084-1089.
Xu et al., "Effects of Early Intervention with Sodium Butyrate on Gut Microbiota and the Expression of Inflammatory Cytokines in Neonatal Piglets", PLoS One, 2016;11(9):e0162461: pp. 1-20.
Chai et al., "GPR109A and vascular inflammation", Cum Atheroscler. Rep. 2013; vol. 15(5):325: pp. 1-10.
Peck-Radosavljevic, 2014, Drug Therapy for Advanced-Stage Liver Cancer, Liver Cancer, 3(2):125-31.
Flores et al., 2014, Emerging Trends in Hepatocellular Carcinoma: Focus on Diagnosis and Therapeutics, Clin Med Insights Oncol, 8:71-6.
Menne et al., 2007, The woodchuck as an animal model for pathogenesis and therapy of chronic hepatitis B virus infection, World J Gastroenterol, 13(1):104-24.
Feitelson et al., 1997, Hepatitis B Virus x Antigen in the Pathogenesis of Chronic Infections and the Development of Hepatocellular Carcinoma, Amer J Pathol, 150:1141-1157.
Tian et al., 2013, Hepatitis B Virus X Protein-Induced Aberrant Epigenetic Modifications Contributing to Human Hepatocellular Carcinoma Pathogenesis, Mol Cell Biol, 33(15):2810-6.
Smith et al., 2013, The microbial metabolites, short chain fatty acids, regulate colonic Treg cell homeostasis, Science, 341(6145):569-73.

Tan et al., 2014, The Role of Short-Chain Fatty Acids in Health and Disease, Adv Immunol, 121:91-119.
Yoo et al., 2008, Hepatitis B virus X protein induces the expression of MTA1 and HDAC1, which enhances hypoxia signaling in hepatocellular carcinoma cells, Oncogene, 27:3405-13.
Park et al., 2015, Short chain fatty acids induce both effector and regulatory T cells by suppression of histone deacetylases and regulation of the mTOR-S6K pathway, Mucosal Immunol, 8(1):80-93.
Celasco et al., 2014, Calcium butyrate: Anti-inflammatory effect on experimental colitis in rats and antitumor properties, Biomed Rep, 2(4):559-563.
Kuroiwa-Trzmielina et al., 2009, Chemoprevention of rat hepatocarcinogenesis with histone deacetylase Inhibitors: Efficacy of tributyrin, a butyric acid prodrug, Int J Cancer, 124(11):2520-7.
De Conti et al., 2012, Chemopreventive effects of the dietary histone deacetylase inhibitor tributyrin alone or in combination with vitamin A during the promotion phase of rat hepatocarcinogenesis, J Nutr Biochem, 23(8):860-6.
Bindels et al., 2012, Gut microbiota-derived propionate reduces cancer cell proliferation in the liver, Br J Cancer, 107(8):1337-44.
Bindels et al., 2013, GPR43/FFA2: physiopathological relevance and therapeutic prospects, Trends Pharmacol Sci, 34(4):226-32.
Mann, 2014, Epigenetics in Liver Disease, Hepatology 60(4):1418-1425.
Endo et al., 2013, Butyrate-Producing Probiotics Reduce Nonalcoholic Fatty Liver Disease Progression in Rats: New Insight into the Probiotics for the Gut-Liver Axis, PLoS One, 8(5):e63388.
Raso et al., 2013, Effects of Sodium Butyrate and Its Synthetic Amide Derivative on Liver Inflammation and Glucose Tolerance in an Animal Model of Steatosis Induced by High Fat Diet, PLoS One 8(7):e68626.
Yadav et al., 2011 "Emerging Role of Antioxidants in the Protection of Uveitis Complications", Curr Med Chem., vol. 18(6): 931-942.
SanGiovanni et al., "The role of omega-3 long-chain polyunsaturated fatty acids in health and disease of the retina", Progress in Retinal and Eye Research 24 (2005) 87-138.
Schmidt et al., "Neurodegenerative Diseases of the Retina and Potential for Protection and Recovery", Current Neuropharmacology, 2008, vol. 6, 164-178.
Chuang et al., "Multiple roles of HDAC inhibition in neurodegenerative conditions", Trends Neurosci. 2009; vol. 32(11): 591-601.
Zhang et al., "Histone Deacetylases Inhibitors in the Treatment of Retinal Degenerative Diseases: Overview and Perspectives", Journal of Ophthalmology Article ID 250812, (2015) 1-9 pages.
Gemenetzi et al., "The role of epigenetics in age-related macular degeneration", Eye (2014) vol. 28, 1407-1417.
Crosson et al., "Inhibition of Histone Deacetylase Protects the Retina from Ischemic Injury", Investigative Ophthalmology & Visual Science, Jul. 2010, vol. 51, No. 7, pp. 3639-3645.
Koriyama et al., "Heat shock protein 70 induction by valproic acid delays photoreceptor cell death by N-methyl-N-nirosourea in mice", 2014, Journal of Neurochemistry, 130:707-719.
Mitton et al., "Different effects of valproic acid on photoreceptor loss in Rd1 and Rd10 retinal degeneration mice", 2014, Molecular Vision, 20:1527-1544.
Thorburn et al., "Evidence that asthma is a developmental origin disease influenced by maternal diet and bacterial metabolites", Nat Commun. 2015; 6:7320; pp. 1-13.
Lynch et al., "The Influence of the Microbiome on Early-Life Severe Viral Lower Respiratory Infections and Asthma—Food for Thought?", Front Immunol, 2017, 8:156; pp. 1-15.
Arrieta et al., "Early infancy microbial and metabolic alterations affect risk of childhood asthma", ScienceTranslationalMedicine, 2015, vol. 7:307ra152; pp. 1-16.
Priyadarshini et al., "Maternal short-chain fatty acids are associated with metabolic parameters in mothers and newborns", Trans Res, 2014, 164(2):153-157.
Zhou et al., "Maternal sodium butyrate supplement elevates the lipolysis in adipose tissue and leads to lipid accumulation in offspring liver of weaning-age rats", Lipids in Health and Disease, 2016, 15:119; pp. 1-8.

(56) References Cited

OTHER PUBLICATIONS

Bonifant et al., "Toxicity and management in CAR T-cell therapy", 2016, Molecular Therapy-Oncolytics, 3:1601; pp. 1-7.
Santini et al., "Induction of apoptosis by monosaccharide butyrate derivatives in chronic lymphocytic leukemia cells", Haematologica, 1999; vol. 84: 897-904.
Arpaia et al., "Metabolites produced by commensal bacteria promote peripheral regulatory T cell generation", 2013, Nature, 504(7480):451-455.
Correa et al., "Regulation of immune cell function by short-chain fatty acids", 2016, Clinical & Translational Immunology, 5:e73: pp. 1-8.
Donohoe et al., "A Gnotobiotic Mouse Model Demonstrates that Dietary Fiber Protects Against Colorectal Tumorigenesis in a Microbiota- and Butyrate—Dependent Manner", 2014, Cancer Discov. 4(12):1387-1397.
Kurita-Ochiai et al., "Volatile Fatty Acid, Metabolic By-Product of Periodontopathic Bacteria, Induces Apoptosis in WEHI 231 and RAJI B Lymphoma Cells and Splenic B Cells", 1998, Infection and Immunity, 66(6):2587-2594.
Astakhova et al., "Short Chain Fatty Acids (SCFA) Reprogram Gene Expression in Human Malignant Epithelial and Lymphoid Cells", 2016, PLoS One, 11(7):e0154102: pp. 1-18.
Cotto et al., "Epigenetic therapy of lymphoma using histone deacetylase inhibitors", 2010, Clin Transl Oncol, 12:401-409.
Kiefer et al., "Mixtures of SCFA, composed according to physiologically available concentrations in the gut lumen, modulate histone acetylation in human HT29 colon cancer cells", British Journal of Nutrition (2006), 96, 803-810.
Merzvinskyte et al., "Effects of Histone Deacetylase Inhibitors, Sodium Phenyl Butyrate and Vitamin B3, in Combination with Retinoic Acid on Granulocytic Differentiation of Human Promyelocytic Leukemia HL-60 Cells", Ann. N.Y. Acad. Sci. 1091: 356-367 (2006).
Santini et al., "Butyrate-stable monosaccharide derivatives induce maturation and apoptosis in human acute myeloid leukaemia cells", British Journal of Haematology, 1998, vol. 101; pp. 529-538.
Miller et al., Clinical Pharmacology of Sodium Butyrate in Patients with Acute Leukemia, European Journal of Can. Clin Oncol., vol. 23, No. 9: 1283-1287 (1987).
McBain et al., "Apoptotic Death in Adenocarcinoma Cell Lines Induced by Butyrate and Other Histone Deacetylase Inhibitors", Biochemical Pharmacology, vol. 53, pp. 1357-1368, (1997).
Novogrodsky et al., "Effect of Polar Organic Compounds on Leukemic Cells", Cancer 51:pp. 9-14 (1983).
Calabresse et al., "Butyric Acid and Its Monosaccharide Ester Induce Apoptosis in the HL-60 Cell Line", Biochemical and Biophysical Research Communications, vol. 195, No. 1: pp. 31-38 (1993).
Jennette, "Overview of the 2012 Revised International Chapel Hill Consensus Conference Nomenclature of Vasculitides", Clin Exp Nephrol., 2013; 17(5): 603-606.
Haghikia et al., "Dietary Fatty Acids Directly Impact Central Nervous System Autoimmunity via the Small Intestine", Immunity vol. 43, 817-829 (2015).
Bhutia et al., "Short, but Smart: SCFAs Train T Cells in the Gut to Fight Autoimmunity in the Brain", (2015) Immunity, 43(4):629-631.
Richards et al., "Dietary metabolites and the gut microbiota: an alternative approach to control inflammatory and autoimmune diseases", Clinical & Translational Immunology (2016) 5, e82: pp. 1-8.

* cited by examiner before after

Photo (before treatment):

Photo (after treatment):

After 45-day regimen

Plaques almost disappeared after 3-5 months

USE OF SHORT CHAIN FATTY ACIDS FOR THE TREATMENT AND PREVENTION OF DISEASES AND DISORDERS

CROSS-REFERENCE TO RELATED APPLICATIONS

This application claims the benefit of priority under 35 U.S.C. 365(c) to International Patent Application No. PCT/US2018/015383, filed on Jan. 26, 2018, which is entitled to priority under 35 U.S.C. § 119(e) to U.S. Provisional Patent Application No. 62/451,192 filed Jan. 27, 2017, U.S. Provisional Patent Application No. 62/510,867 filed May 25, 2017, U.S. Provisional Patent Application No. 62/510,872 filed May 25, 2017, U.S. Provisional Patent Application No. 62/530,371 filed Jul. 10, 2017, U.S. Provisional Patent Application No. 62/539,572 filed Aug. 1, 2017, and U.S. Provisional Patent Application No. 62/588,961 filed Nov. 21, 2017, the disclosures of which are incorporated herein by reference in their entirety.

BACKGROUND OF THE INVENTION

Short chain fatty acids (SCFAs) are the main metabolic products of anaerobic bacteria fermentation in the intestine, and have been shown to modulate different processes (such as metabolic functions and homeostasis) in the gastrointestinal (GI) tract in adipose tissue, immune and nervous systems. Quantitative and qualitative changes in the gut microbiome and, consequently, changes in the concentrations of the produced metabolites have been suggested to promote the development of pathological conditions including inflammatory bowel disease (IBD), colon cancer, obesity and type 1 and 2 diabetes mellitus.

SCFAs are saturated aliphatic acids consisting of one polar carboxylic acid moiety and hydrophobic hydrocarbon chain among which acetate (C2), propionate (C3) and butyrate (C4) are the most common and well-studied molecules.

The SCFAs affect several cellular processes including gene expression, chemotaxis, differentiation, proliferation and apoptosis via activation of G protein coupled receptors (GPCRs), inhibition of histone deacetylases (HDACs) and by binding to the butyrate-responsive elements in the gene promoter regions of some transcriptional factors (which may explain the pleiotropic effects of butyrate). SCFAs are important regulators of inflammation by controlling migration of immune cells toward inflammatory sites as well as modulating their activation state. Importantly, SCFAs influence the balance between pro- and anti-inflammatory cells and serve as a means of communication between microbiota and the immune system. The principle mechanisms through which SCFAs exert anti-inflammatory effects are suppression of TNFα and NF-κB activation, the inhibition of IFN-γ production, and upregulation of the peroxisome proliferator-activated receptor γ (PPARγ, a nuclear hormone receptor capable to inhibit NF-κB dependent transcriptional activation.)

Current SCFA therapeutic compounds have limited or inadequate efficacy because of the rapid absorption in the small intestine and a very short half-life. Thus there is a need in the art for safe effective compositions comprising SCFA for use in the treatment or prevention of diseases and disorders. The present invention addresses this unmet need.

SUMMARY OF THE INVENTION

In one embodiment, the invention relates to a composition comprising at least one compound selected from the group consisting of: a short chain fatty acid (SCFA), a SCFA precursor, a SCFA biosynthesis precursor, a compound comprising a SFCA moiety, a derivative thereof, and a combination thereof.

In one embodiment, the composition comprises at least one SCFA moiety linked to at least one additional moiety.

In one embodiment, the at least one additional moiety comprises polyethylene glycol (PEG).

In one embodiment, the composition hydrolyzes under a low pH condition to yield PEG and a SCFA.

In one embodiment, the SCFA or SCFA moiety comprises at least one selected from the group consisting of: acetic acid, butyric acid (BA), C3-C12 fatty acids, C3-C10 fatty acids, C3-C8 fatty acids, methoxyacetic acid, valproic acid (VPA), propionic acid, 3-methoxypropionic acid, ethoxyacetic acid, formic acid, isobutyric acid, tributyrin, butyrate, propionate, N-acetylbutyrate (as well as other forms of butyrate, e.g., phenylbutyrate, isobutyrate, pivaloyloxymethyl butyrate, monoacetone glucose 3-butyrate), isovaleric acid, valeric acid, isocaproic acid, caproic acid, lactic acid, succinic acid, pyruvic acid, octanoic acid, dodecanoic acid, (4R)-4-hydroxypentanoic acid, 2-ethylhydracrylic acid, 2-hydroxy-3-methylpentanoate, 2-hydroxy-3-methylpentanoic acid, 2-methylbut-2-enoic acid, 2-oxobutanoic acid, 3-hydroxypentanoic acid, 3-methylbut-2-enoic acid, butenoic acid, methylbutyric acid, dimethylbutyric acid, pentadienoic acid, pentenoic acid, pivalic acid, propynoic acid and a combination thereof.

In one embodiment, the SCFA precursor or SCFA precursor moiety of the SCFA precursor derivative comprises at least one selected from the group consisting of: a salt of lactate, a salt of succinate, a salt of formate, 1,2-propenedol, trypamine, indole, indole-3-acetate, and a combination thereof.

In one embodiment, the SCFA biosynthesis precursor or SCFA biosynthesis precursor moiety of the SCFA biosynthesis precursor derivative comprises an acetyl-CoA carboxylase inhibitor, an adenosine monophosphate kinase (AMPK) activator, vitamin D, or a combination thereof.

In one embodiment, the composition comprises butyrate.

In one embodiment, the composition comprises at least two SCFAs.

In one embodiment, the composition comprises butyrate and propionate.

In one embodiment, the invention relates to a pharmaceutical composition comprising at least one compound selected from: a short chain fatty acid (SCFA), a SCFA precursor, a SCFA biosynthesis precursor, a compound comprising a SFCA moiety, a derivative thereof, and a combination thereof.

In one embodiment, the pharmaceutical composition comprises at least one SCFA moiety linked to at least one additional moiety. In one embodiment, the at least one additional moiety comprises polyethylene glycol (PEG).

In one embodiment, the pharmaceutical composition hydrolyzes under a low pH condition to yield PEG and a SCFA.

In one embodiment, the SCFA or SCFA moiety comprises at least one selected from the group consisting of: acetic acid, butyric acid (BA), C3-C12 fatty acids, C3-C10 fatty acids, C3-C8 fatty acids, methoxyacetic acid, valproic acid (VPA), propionic acid, 3-methoxypropionic acid, ethoxyacetic acid, formic acid, isobutyric acid, tributyrin, butyrate, propionate, N-acetylbutyrate (as well as other forms of butyrate, e.g., phenylbutyrate, isobutyrate, pivaloyloxymethyl butyrate, monoacetone glucose 3-butyrate), isovaleric acid, valeric acid, isocaproic acid, caproic acid, lactic acid, succinic acid, pyruvic acid, octanoic acid, dodecanoic acid, (4R)-4-hydroxypentanoic acid, 2-ethylhydracrylic acid, 2-hydroxy-3-methylpentanoate, 2-hydroxy-3-methylpentanoic acid, 2-methylbut-2-enoic acid, 2-oxobutanoic acid, 3-hydroxypentanoic acid, 3-methylbut-2-enoic acid, butenoic acid, methylbutyric acid, dimethylbutyric acid, pentadienoic acid, pentenoic acid, pivalic acid, propynoic acid and a combination thereof.

In one embodiment, the SCFA precursor or SCFA precursor moiety of the SCFA precursor derivative comprises at least one selected from the group consisting of: a salt of lactate, a salt of succinate, a salt of formate, 1,2-propenedol, trypamine, indole, indole-3-acetate, and a combination thereof.

In one embodiment, the SCFA biosynthesis precursor or SCFA biosynthesis precursor moiety of the SCFA biosynthesis precursor derivative comprises an acetyl-CoA carboxylase inhibitor, an adenosine monophosphate kinase (AMPK) activator, vitamin D, or a combination thereof.

In one embodiment, the pharmaceutical composition comprises 100 milligrams (mg) to 6 grams (g) of at least one SCFA.

In one embodiment, the pharmaceutical composition comprises butyrate. In one embodiment, the pharmaceutical composition comprises 900 to 1800 mg butyrate.

In one embodiment, the pharmaceutical composition comprises at least two SCFAs.

In one embodiment, the pharmaceutical composition comprises butyrate and propionate. In one embodiment, the pharmaceutical composition comprises 900 to 1800 mg butyrate and 100 mg to 200 mg propionate.

In one embodiment, the pharmaceutical composition further comprises a pharmaceutically acceptable excipient.

In one embodiment, the pharmaceutical composition is an enteric coated, extended release capsule.

In one embodiment, the pharmaceutical composition comprises 900 mg butyrate, 100 mg propionate, 10 mg apremilast, 10 mg magnesium, and 50 IU vitamin D3.

In one embodiment, the pharmaceutical composition is formulated as an eyedrop. In one embodiment, the eyedrop comprises 10 micromolar ($\mu$M) to 100 $\mu$M butyrate. In one embodiment, the eyedrop comprises 10 $\mu$M to 100 $\mu$M propionate. In one embodiment, the eyedrop comprises 10 $\mu$M to 100 $\mu$M butyrate and 10 to 100 $\mu$M propionate.

In one embodiment, the invention relates to a method for treating or preventing a disease or disorder, comprising administering to a subject a composition or pharmaceutical composition comprising at least one compound selected from: a short chain fatty acid (SCFA), a SCFA precursor, a SCFA biosynthesis precursor, a compound comprising a SFCA moiety, a derivative thereof, and a combination thereof.

In one embodiment, the disease or disorder is a skin disease or disorder, an allergic or autoimmune disease or disorder, an eye disease or disorder, an adverse effect associated with immunotherapy, cancer or a combination thereof.

In one embodiment, the method comprises administering a composition or pharmaceutical composition comprising 100 mg to 6 g butyrate.

In one embodiment, the method comprises administering the composition or pharmaceutical composition daily for at least one week.

In one embodiment, the method comprises administering the composition or pharmaceutical composition one to three times daily for at least one week.

In one embodiment, the method comprises further comprising administering at least one additional treatment or therapeutic agent to the subject.

In one embodiment, the at least one additional treatment is immunotherapy.

In one embodiment, the invention relates to a method for treating or preventing a skin disease or disorder, comprising administering a composition comprising at least 900 mg of butyrate and at least 100 mg propionate in enteric coated, extended release capsules, 3 times/day for at least 2 weeks. In one embodiment, the method further comprises administering a dose of at least 900 mg of butyrate, twice a day for at least 2 weeks, following the completion of the first dosage regimen.

In one embodiment, the invention relates to a method for treating or preventing a skin disease or disorder, comprising administering a dose of at least 900 mg of butyrate, at least 100 mg propionate, and at least 10 mg apremilast in enteric coated, extended release capsules, 3 times/day for at least 2 weeks.

In one embodiment, the invention relates to a method for treating or preventing an eye disease or disorder comprising: administering a daily oral dose of at least 4 g of butyrate and at least 1.5 g propionate in enteric coated, extended release capsules, 3 times/day for at least 2 weeks.

In one embodiment, the invention relates to a method for treating or preventing an eye disease or disorder comprising administering eyedrops containing at least 20 $\mu$M of butyrate and at least 10 $\mu$M propionate at least 2 times/day for at least 3 days.

In one embodiment, the invention relates to a method for treating or preventing an adverse effect associated with immunotherapy comprising administering a daily oral dose of at least 5 g of butyrate and at least 2 g propionate in enteric coated, extended release capsules, 3 times/day for at least 2 weeks. In one embodiment, the administering is performed prior to an immunotherapy, concurrent with an immunotherapy, subsequent to an immunotherapy, or a combination thereof.

In one embodiment, the invention relates to a method for treating or preventing an allergic disease, an autoimmune disease or asthma comprising: administering a daily oral dose of at least 1 of butyrate, at least 0.5 g propionate, and at least 0.5 g acetate in enteric coated, extended release capsules, 3 times/day for at least 2 weeks.

In one embodiment, the invention relates to a method for treating or preventing an allergic disease, an autoimmune disease and asthma in a C-section delivered neonate comprising: administering to the neonate a daily oral dose of at least 80 mg of butyrate, at least 20 mg propionate, and at least 20 mg acetate as a nutraceutical.

In one embodiment, the invention relates to a method for treating or preventing vasculitis comprising administering a daily oral dose of at least 5 g of butyrate in enteric coated, extended release capsules, 3 times/day for at least 2 weeks. In one embodiment, the method further comprises administering a daily oral dose of at least 3 g of butyrate, twice a day for at least 2 weeks, following the completion of the first dosage regimen.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 2, comprising FIG. 2A depicts images of the patient's left elbow before and after treatment. FIG. 2B depicts images of the patient's right elbow before and after treatment. FIG. 2C depicts an image of the re-emergence of psoriasis on the patient's left elbow after 20 days the patient ceased the butyrate treatment regimen.

FIG. 5, comprising FIG. 5A depicts images of the patient's left hip before and after treatment the second treatment regimen. FIG. 5B depicts images of the patient's right hip before and after the second treatment regimen. FIG. 5C depicts images of the patient's tailbone before and after the second treatment regimen.

DETAILED DESCRIPTION

Figure 1:
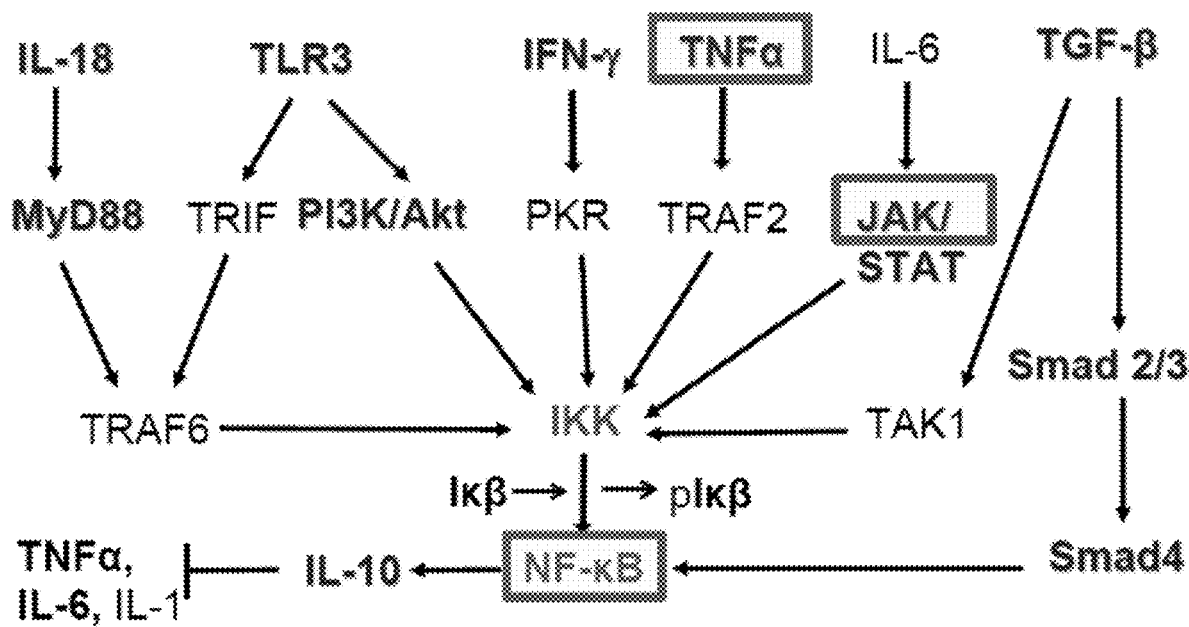
FIG. 1 depicts a diagram showing signaling pathways that are affected by SCFAs. Of the proteins included on the diagram, IL-18, TLR3, IFN-γ, TNFα, TGF-β, MyD88, PI3K/Akt, JAK/STAT, Smad 2/3, Smad 4 and IL-10 were found to be downregulated by SCFA treatment. The levels of IL-6, TRIF, PKR, TRAF2, TAK1 and TRAF6 were not evaluated for this study.

In one embodiment, the invention relates to compositions comprising at least one SCFA for the treatment or prevention of one or more diseases and/or disorders in a subject.

In one embodiment, the SCFA comprises at least one selected from the group including, but not limited to: a SCFA, a SCFA precursor, a SCFA biosynthesis precursor, a compound comprising a SCFA moiety, a derivative thereof, a salt thereof, an ester thereof, a conjugate base thereof (for example, PEGylated conjugates), and a combination thereof. In one embodiment, a SCFA or SCFA moiety includes, but is not limited to, acetic acid, butyric acid (BA), C3-C12 fatty acids, C3-C10 fatty acids, C3-C8 fatty acids, methoxyacetic acid, valproic acid (VPA), propionic acid, 3-methoxypropionic acid, ethoxyacetic acid, formic acid, isobutyric acid, tributyrin, butyrate, propionate, N-acetylbutyrate (as well as other forms of butyrate, e.g., phenylbutyrate, isobutyrate, pivaloyloxymethyl butyrate, monoacetone glucose 3-butyrate), isovaleric acid, valeric acid, isocaproic acid, caproic acid, lactic acid, succinic acid, pyruvic acid, octanoic acid, dodecanoic acid, (4R)-4-hydroxypentanoic acid, 2-ethylhydracrylic acid, 2-hydroxy-3-methylpentanoate, 2-hydroxy-3-methylpentanoic acid, 2-methylbut-2-enoic acid, 2-oxobutanoic acid, 3-hydroxypentanoic acid, 3-methylbut-2-enoic acid, butenoic acid, methylbutyric acid, dimethylbutyric acid, pentadienoic acid, pentenoic acid, pivalic acid, propynoic acid and a combination thereof. In one embodiment, the SCFA or SCFA moiety includes compounds or structures with at least 12 carbon atoms, at least 11 carbon atoms, at least 10 carbon atoms, at least 9 carbon atoms, at least 8 carbon atoms, at least 7 carbon atoms, at least 6 carbon atoms, at least 5 carbon atoms, at least 4 carbon atoms, at least 3 carbon atoms, and at least 2 carbon atoms. In one embodiment, the SCFA or SCFA moiety is not a branched fatty acid. In one embodiment, the SCFA or SCFA moiety includes compounds or structures with less than 13 carbon atoms, less than 12 carbon atoms, less than 11 carbon atoms, less than 10 carbon atoms, less than 9 carbon atoms, less than 8 carbon atoms, or less than 7 carbon atoms. In one embodiment, the SCFA or SCFA moiety is not a branched fatty acid. In one embodiment, the SCFA or SCFA moiety is a branched fatty acid.

In one embodiment, the invention relates to methods for the treatment or prevention of one or more diseases and/or disorders in a subject, comprising administering to a subject at least one composition comprising a SCFA. In one embodiment, at least one composition comprising a SCFA is administered to a subject in combination with at least one additional agent or therapy, for the treatment or prevention of a disease and/or disorder in a subject. In one embodiment, at least one SCFA and at least one additional therapeutic agent are administered together in one composition. In one embodiment, at least one SCFA and at least one additional therapeutic agent are administered separately, as two or more compositions.

In one embodiment, a subject is a human. In one embodiment, a subject is a non-human animal.

Definitions

It is to be understood that the figures and descriptions of the present invention have been simplified to illustrate elements that are relevant for a clear understanding of the present invention, while eliminating, for the purpose of clarity, many other elements found in the invention. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein.

The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "adverse effect of cancer immunotherapy," as used herein, may refer to at least one of the following types of adverse effect of cancer immunotherapy: cytokine release syndrome (CRS), neurological toxicity, on-target/off-tumor recognition, anaphylaxis, graft versus host disease (GVHD), off-target antigen recognition, and macrophage activation syndrome (MAS).

By "allergy" or "allergic disease or disorder" is meant one or more of a number of conditions caused by hypersensitivity of the immune system to one or more substances in the environment.

A subject is "at risk for" developing a condition if there is an increased probability that the individual will develop the condition compared to a population (e.g., the general population, an age-matched population, a population of the same sex). The increased probability can be due to one or a combination of factors including the presence of specific alleles/mutations of a gene or exposure to a particular environment.

By an "autoimmune disease or disorder" is meant an immune response against a self-antigen that results in inflammation or destruction of healthy tissue in a subject. Desirably the subject is a mammal, such as a human. Exemplary autoimmune diseases include, but are not limited to, arthritis (e.g., rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, psoriasis vulgaris, inverse psoriasis, erythrodermic psoriasis, seborrheic psoriasis and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis, respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and auto-immune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, lymphoid interstitial pneumonitis, bronchiolitis obliterans (non-transplant) vs NSIP, Guillain-Barre syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia areata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, fibrosis of any organ or tissue, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis *acuta*, pyoderma gangrenosum, Quervain's thyreoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as *Leishmania*, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis. Other examples of autoimmune diseases may be disclosed elsewhere herein.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, bladder cancer, renal cancer, brain cancer, lymphoma, leukemia, lung cancer and the like.

As used herein, "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., a human).

The term "combination therapy", as used herein, refers to the administration of two or more therapies, two or more therapeutic agents, or a combination of at least one therapeutic agent and at least one method of therapy, such as radiation, immunotherapy, and chemotherapy.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "human microbiome" refers to the totality of microbes, their genetic elements (genomes), and environmental interactions in the human body.

The term "immune response" encompasses both cellular and humoral immune responses, including stimulating the production of cytokines, stimulating the proliferation of immune cells, stimulating the activation of immune cells, or stimulating the lytic activity of immune cells. Examples of immune responses stimulated by the methods of the invention are the secretion of cytokines, the activation of NK cells, the proliferation of B cells, T cells, macrophages, monocytes, and other immune cells, and other immune responses. To detect a cellular immune response, for example, T cell effector activity against cells expressing the antigen can be detected using standard assays, e.g., target-cell killing, macrophage activation, B-cell activation or lymphokine production. Humoral responses can be measured by detecting the appearance of, or the increase in titer of, for example, antigen-specific antibodies, using methods known in the art, such as ELISA. The progress of the antibody response can be determined by measuring class switching, such as the switch from an early IgM response to a later IgG response.

The term "inhibit," as used herein, means to suppress or block an activity or function by at least about ten percent relative to a control value. As an example, the activity is suppressed or blocked by 50% compared to a control value, by 75%, or by 95% or more.

The term "psoriasis" as used herein includes at least seven types of psoriasis: plaque psoriasis, guttate psoriasis, inverse psoriasis, pustular psoriasis, psoriasis vulgaris, seborrheic psoriasis erythrodermic psoriasis, nail psoriasis, and psoriatic arthritis.

The term "regulatory T cells" or "Tregs" refers to T cells that suppress an abnormal or excessive immune response and play a role in immune tolerance. The regulatory T cells are typically transcription factor Foxp3-positive CD4-positive T cells. The regulatory T cells of the present invention also include transcription factor Foxp3-negative regulatory T cells that are IL-10-producing CD4-positive T cells.

The term "induces proliferation or accumulation of regulatory T cells" refers to an effect of inducing the differentiation of immature T cells into regulatory T cells, which differentiation leads to the proliferation and/or the accumulation of regulatory T cells. Further, the meaning of "induces proliferation or accumulation of regulatory T cells" includes in-vivo effects, in vitro effects, and ex vivo effects.

The term "uveitis" as used herein refers to inflammation of the eye that may affect the uvea, or middle layer of the eye but also the lens, retina, optic nerve, and vitreous chamber. Uveitis (pronounced you-vee-EYE-tis) may be inflammation of the uvea, the middle layer of the eye that includes the iris, ciliary body and choroid. Uveitis can be caused by (1) autoimmune disorders (due to aberrant T cell-mediated responses triggered by inflammation and directed against retinal or cross-reactive antigens), (2) infections, (3) trauma, or (4) could be idiopathic (unknown cause). The type of uveitis is classified by where inflammation occurs in the uvea. Anterior uveitis is inflammation of the iris (iritis) or the iris and ciliary body. Intermediate uveitis is inflammation of the ciliary body. Posterior uveitis is inflammation of the choroid. Diffuse uveitis (also called panuveitis) is inflammation of all areas of the uvea. Uveitis may involve the full eye (panuveitis) or a segment of the eye (anterior, intermediate or posterior). Examples of uveitis include, but are not limited to, anterior uveitis (comprising iritis, iridiocyclitis, and anterior cylitis), intermediate uveitis (comprising pars planitis, posterior cyclitis, and hyalitis), posterior uveitis (comprising focal, multifocal or diffuse choroiditis, chorioretinitis, retinochoroiditis, retinitis, and neuroretinitis), panuveitis, acute uveitis, recurring uveitis and chronic uveitis. In one embodiment, uveitis is non-infectious uveitis. Examples of causes of non-infectious uveitis include, but are not limited to systemic autoimmune disorders (such as, for example Behcet's disease and Vogt-Koyanagi-Harada (VKH) disease); trauma and surgery. In one example, non-infectious uveitis is idiopathic non-infectious uveitis.

The terms "tolerance" and "immune tolerance" refer to the process by which the immune system does not attack an antigen.

The terms "tolerance induction" or "inducing tolerance" refer to a process by which tolerance to external antigens can be created by manipulating the immune system.

The terms "treatment", "treating" and the like are used herein to generally mean obtaining a desired pharmacological and/or physiological effect. The effect may be prophylactic in terms of completely or partially preventing a disease or disorder, or a symptom thereof, and/or may be therapeutic in terms of partially or completely curing a disease or disorder, and/or adverse effect attributed to the disease or disorder. The term "treatment" as used herein includes any treatment of a disease or disorder in a subject and includes: (a) preventing a disease or disorder from occurring in a subject which may be predisposed to the disease or disorder; (b) inhibiting the disease or disorder, i.e. arresting its development: or (c) relieving the disease or disorder, i.e. causing regression of the disease or disorder.

The terms "effective amount" and "pharmaceutically effective amount" refer to a sufficient amount of an agent to provide a desired biological result. That result can be reduction and/or alleviation of a sign, symptom, or cause of a disease or disorder, or any other desired alteration of a biological system.

The term "leukemia," as used herein, may refer to at least one of the following types of leukemia: myeloproliferative neoplasms (MPNs), polycythemia vera (PV), essential thrombocytosis (ET), idiopathic/myelofibrosis (MF), acute myeloid leukemia (AML), and childhood acute lymphoblastic leukemia (ALL). The term "leukemia" may also refer generally to cancer of blood forming tissue, or to blood cancer.

The term "microbiota" refers, collectively, to the entirety of microbes found in association with a higher organism, such as a human.

A "therapeutically effective amount" refers to that amount which provides a therapeutic effect for a given condition and administration regimen. In particular, "therapeutically effective amount" means an amount that is effective to prevent, alleviate or ameliorate symptoms of a disease or disorder, or prolong the survival of the subject being treated, which may be a human or non-human animal.

The term "macular degeneration" as used herein refers to any and all forms of macular degeneration, including "wet" and "dry" macular degeneration. There are two types of age-related macular degeneration (AMD): the dry (atrophic) form and the wet (exudative) form. The dry form of AMD affects about 90 percent of AMD patients and usually begins with the formation of tiny yellow deposits called drusen in the macula. Drusen usually do not cause serious loss of vision, but can cause distortion of vision. However, for reasons that are not yet understood, sometimes drusen will cause the macula to thin and break down, slowly leading to vision loss. The wet form of AMD occurs in about 10 percent of AMD patients. It is caused by the growth of abnormal blood vessels beneath the macula that can leak fluid and blood to form exudate. The wet form of AMD typically causes significant vision problems in the affected eye and can progress very rapidly, causing permanent central vision loss.

As used herein, the term "pharmaceutical composition" refers to a mixture of at least one compound of the invention with other chemical components and entities, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent, or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol, polyethylene glycol and glycerol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The term "neonate" as used herein generally refers to an infant or a young mammal, e.g., a human being.

The term "nutritional composition" may refer to a food product intended for human consumption, for example, a beverage, a drink, a bar, a snack, an ice cream, a dairy product, for example a chilled or a shelf-stable dairy product, a fermented dairy product, a drink, for example a milk-based drink, an infant formula, a growing-up milk, a confectionery product, a chocolate, a cereal product such as a breakfast cereal, a sauce, a soup, an instant drink, a frozen product intended for consumption after heating in a microwave oven or a conventional oven, a ready-to-eat product, a fast food or a nutritional formula.

The terms "patient," "subject," "individual," and the like are used interchangeably herein, and refer to any animal, or cells thereof whether in vitro or in situ, amenable to the methods described herein. The patient, subject, or individual may be a human or a non-human animal.

As used herein, the term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be included on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject.

"Instructional material," as that term is used herein, includes a publication, a recording, a diagram, or any other medium of expression which can be used to communicate the usefulness of components of the invention in a kit for identifying or alleviating or treating the various diseases or disorders recited herein. Optionally, or alternately, the instructional material may describe one or more methods of identifying or alleviating the diseases or disorders in a cell or a tissue of a subject. The instructional material of the kit may, for example, be affixed to a container that contains the compositions of the invention or be shipped together with a container that contains the compositions of the invention. Alternatively, the instructional material may be shipped separately from the container with the intention that the recipient uses the instructional material and the composition cooperatively.

The term "lymphoma," as that term is used herein, may refer to at least one of the following types of lymphoma: activated B-cell-like diffuse large B cell lymphoma (ABC DLBCL), follicular lymphoma (FL), mucosa associated lymphoid tissue lymphoma (MALT), Hodgkin lymphoma (HL), and primary mediastinal B cell lymphoma (PMBL).

"Short chain fatty acids" (SCFA) are fatty acids typically with aliphatic tails shorter than aliphatic tails of long chain fatty acids. As used herein, the term short chain fatty acid may also refer to salts or esters of fatty acids, especially pharmaceutically acceptable salts and esters of fatty acids (e.g., sodium butyrate, arginine butyrate).

As used herein, the term "stimulate an immune response" includes stimulating, eliciting, increasing, enhancing, sustaining, and/or improving the stimulation of new immune response or of a preexisting immune response. Thus, "stimulating an immune response" as an immunotherapy refers to enhancing the therapeutic efficacy, increasing survival time, slowing the progression of a cancerous tumor or shrinking the cancerous tumor size, preventing the spread of a tumor or of metastases, preventing or slowing the recurrence of treated cancer, eliminating cancer cells not killed by earlier treatments, targeting potential cancer cells or targeting antigens derived from a virus associated with cancer. In the methods of this invention, the immunotherapeutic agent and the compound of selected from formulae (I), (II), (III), (IV) and (V) are administered in an amount effective to stimulate an immune response in the subject individual at a dose sufficient to generate an effective immune response without unacceptable toxicity. As will be understood by one of skill in the art, the magnitude of the immune response and the maintenance of that response may have varying degrees which will be recognized a having a potential therapeutic or prophylactic benefit.

The term "vasculitis," as that term is used herein, may refer to at least one of the following types of vasculitis: giant cell arteritis, Takayasu disease, Churg-Strauss syndrome, Wegener granulomatosis, microscopic polyangiitis, essential cryoglobulinemic vasculitis, Henoch-Shoenlein purpura, Kawasaki disease, polyarteritis nodosa, anti-neutrophil cytoplasmic antibody vasculitis, and necrotizing and cresentic glomerulonephritis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based, in part upon the discovery that short chain fatty acids (SCFA) serve as modulators of multiple cellular signaling proteins, including, but not limited to, IL-18, TLR3, IFN-γ, TNFα, TGF-β, MyD88, PI3K/Akt, JAK/STAT, Smad 2/3, Smad 4, IL-10, Notch, hedgehog, Wnt (beta-catenin), matrix metalloproteinases 9 and 10, tissue inhibitor of metalloproteinases, nodal and NF-κB signaling. In various embodiments, the signaling proteins that are modulated by SCFAs themselves modulate biological pathways or processes including, but not limited to, inflammation, immunity, proliferation, differentiation, apoptosis, oncogenesis, transcription of DNA, cytokine production, cell survival, angiogenesis, fibrogenesis and cellular responses to stimuli such as stress, cytokines, free radicals, heavy metals, and ultraviolet irradiation In one embodiment, the invention relates to compositions comprising at least one SCFA and methods of use for treating or preventing medical diseases or disorders characterized by elevated levels or abnormal expression of at least one of IL-18, TLR3, IFN-γ, TNFα, TGF-β, MyD88, PI3K/Akt, JAK/STAT, Smad 2/3, Smad 4 or IL-10 signaling. In one embodiment, the invention relates to compositions comprising at least one SCFA and methods of use for treating or preventing medical diseases or disorders characterized by decreased levels or abnormal expression of NF-κB signaling.

Compositions

In one embodiment, the invention provides compositions comprising at least one short chain fatty acid (SCFA), SCFA precursor, SCFA biosynthesis precursor, a derivative thereof, a SCFA moiety or a combination thereof.

In one embodiment, the composition of the invention comprises at least one SCFA, or a compound comprising a SCFA moiety. In one embodiment, a SCFA or SCFA moiety includes, but is not limited to, acetic acid, butyric acid (BA), C3-C12 fatty acids, C3-C10 fatty acids, C3-C8 fatty acids, methoxyacetic acid, valproic acid (VPA), propionic acid, 3-methoxypropionic acid, ethoxyacetic acid, formic acid, isobutyric acid, tributyrin, N-acetylbutyrate (as well as other forms of butyrate, e.g., phenylbutyrate, isobutyrate, pivaloyloxymethyl butyrate, monoacetone glucose 3-butyrate), isovaleric acid, valeric acid, isocaproic acid, caproic acid, lactic acid, succinic acid, pyruvic acid, octanoic acid, dodecanoic acid, (4R)-4-hydroxypentanoic acid, 2-ethylhydracrylic acid, 2-hydroxy-3-methylpentanoate, 2-hydroxy-3-methylpentanoic acid, 2-methylbut-2-enoic acid, 2-oxobutanoic acid, 3-hydroxypentanoic acid, 3-methylbut-2-enoic acid, butenoic acid, methylbutyric acid, dimethylbutyric acid, pentadienoic acid, pentenoic acid, pivalic acid, propynoic acid and a combination thereof. In one embodiment, the SCFA or SCFA moiety includes compounds or structures with at least 12 carbon atoms, at least 11 carbon atoms, at least 10 carbon atoms, at least 9 carbon atoms, at least 8 carbon atoms, at least 7 carbon atoms, at least 6 carbon atoms, at least 5 carbon atoms, at least 4 carbon atoms, at least 3 carbon atoms, and at least 2 carbon atoms. In one embodiment, the SCFA or SCFA moiety includes compounds or structures with less than 13 carbon atoms, less than 12 carbon atoms, less than 11 carbon atoms, less than 10 carbon atoms, less than 9 carbon atoms, less than 8 carbon atoms, or less than 7 carbon atoms. In one embodiment, the SCFA or SCFA moiety is not a branched fatty acid. In one embodiment, the SCFA or SCFA moiety is a branched fatty acid.

In one embodiment, the composition of the invention comprises at least one compound comprising a precursor of a SCFA, or a moiety thereof. In one embodiment, the precursor, or moiety thereof, is selected from the group including, but not limited to, plant cell-wall polysaccharides, dietary nonstarch polysaccharides (NSP) a salt of lactate, a salt of succinate, a salt of formate, 1,2-propenedol, trypamine, indole, indole-3-acetate, and a combination thereof.

In one embodiment, the composition of the invention comprises at least one compound comprising a biosynthesis precursor of a SCFA, or a moiety thereof. In one embodiment, the biosynthesis precursor, or moiety thereof, is selected from the group including, but not limited to an acetyl-CoA carboxylase inhibitor, an adenosine monophosphate kinase (AMPK) activator, vitamin D, and a combination thereof.

In one embodiment, the composition of the invention comprises a salt of a SCFA, or a derivative thereof. For example, a salt of butyric acid may be one or more of sodium butyrate, magnesium butyrate or calcium butyrate. In one embodiment, the composition comprises one or more of magnesium butyrate and calcium butyrate.

In one embodiment, the composition of the invention comprises a derivative of a SCFA. In one embodiment, the derivative comprises at least one SCFA moiety linked to at least one additional moiety. In one embodiment, the derivative comprises at least one SCFA moiety linked to at least one polyethylene glycol (PEG) moiety. In one embodiment, the at least one SCFA moiety linked to at least one PEG moiety hydrolyzes under a low pH condition to yield at least one SCFA molecule and at least one PEG molecule.

In one embodiment, the composition of the invention comprises a combination of SCFAs, and/or derivatives thereof. In one embodiment, the composition is prepared at amounts of at least 10 mM, at least 20 mM, at least 30 mM, 40 mM, 50 mM, 60 mM, 70 mM, 80 mM, 90 mM, 100 mM, or more of each or all the compounds of the composition.

Derivatives of SCFAs, e.g., having substituents on the carbon chain such as O, S, N, methyl, ethyl, halogen, and other groups that do not interfere with the compound's therapeutic activity may also be used to form the compositions of this invention. In one embodiment, the compound of the invention comprises at least one SCFA linked to at least one additional moiety, such as O, S, N, methyl, ethyl, halogen, and other groups that do not interfere with the compound's therapeutic activity.

In some instances, the SCFA of the invention can be pegylated. Polyethylene glycol (PEG) has been widely used in biomaterials, biotechnology and medicine primarily because PEG is a biocompatible, nontoxic, nonimmunogenic and water-soluble polymer (Zhao and Harris, ACS Symposium Series 680: 458-72, 1997). In the area of drug delivery, PEG derivatives have been widely used in covalent attachment (i.e., "PEGylation") to proteins to reduce immunogenicity, proteolysis and kidney clearance and to enhance solubility (Zalipsky, Adv. Drug Del. Rev. 16:157-82, 1995). Similarly, PEG has been attached to low molecular weight, relatively hydrophobic drugs to enhance solubility, reduce toxicity and alter biodistribution. Typically, PEGylated drugs are injected as solutions. However, they may be administered orally, or by another route.

A closely related application is synthesis of crosslinked degradable PEG networks or formulations for use in drug delivery since much of the same chemistry used in design of degradable, soluble drug carriers can also be used in design of degradable gels (Sawhney et al., Macromolecules 26: 581-87, 1993). It is also known that intermacromolecular complexes can be formed by mixing solutions of two complementary polymers. Such complexes are generally stabilized by electrostatic interactions (polyanion-polycation) and/or hydrogen bonds (polyacid-polybase) between the polymers involved, and/or by hydrophobic interactions between the polymers in an aqueous surrounding (Krupers et al., Eur. Polym J. 32:785-790, 1996). For example, mixing solutions of polyacrylic acid (PAAc) and polyethylene oxide (PEO) under the proper conditions results in the formation of complexes based mostly on hydrogen bonding. Dissociation of these complexes at physiologic conditions has been used for delivery of free drugs (i.e., non-PEGylated). In addition, complexes of complementary polymers have been formed from both homopolymers and copolymers.

In one embodiment, the composition of the invention comprises a precursor of a SCFA alone or in combination with one or more SCFAs. Precursors of SCFAs include, but are not limited to, a salt of formate, a salt of lactate, a salt of succinate, 1,2-propenedol, trypamine, indole, and indole-3-acetate.

In one embodiment, the composition of the invention comprises a precursor of SCFA biosynthesis alone or in combination with one or more SCFA. Precursors of SCFA biosynthesis include, but are not limited to, a salt of formate, a salt of lactate, a salt of succinate, acetyl-CoA carboxylase inhibitors, adenosine monophosphate kinase (AMPK) activators, and vitamin D.

SCFAs stimulate T regulatory (Treg) cell function, which accounts for some of their anti-inflammatory properties. Given that inhibitors of acetyl-CoA carboxylase also promote Treg cell function, in one embodiment, a composition comprises an inhibitor of acetyl-CoA carboxylase, including but not limited to, biotin or its naturally or chemically synthesized analogs (which are acetyl-CoA carboxylase inhibitors) alone or in combination with one or more other SCFAs, to stimulate Treg functions.

In various embodiments, a compound comprising at least one SCFA, or a compound comprising a SCFA moiety of the invention may be combined with one or more compounds, such as one or more additional therapeutic agent, for a particular disease or disorder. In one embodiment, the one or more SCFAs of the invention may be in the same composition as one or more additional therapeutic agent. In various embodiments the composition may comprise at least 1, at least 2, at least 3, at least 4, at least 5, at least 6, at least 7, at least 8, at least 9, at least 10 or more than 10 additional therapeutic agents. Exemplary additional therapeutic agents and/or compounds that can be included in a composition of the invention are discussed in detail elsewhere herein.

Methods

The present invention provides methods for treating or preventing a mammalian disease in a subject in need thereof by administration to said subject a therapeutically effective amount of the compositions of the present invention.

General examples of target diseases for which the composition(s) is/are useful for treatment (reducing adverse effects or prevention) include autoimmune diseases, allergic diseases, infectious diseases, and rejection in organ transplantations, such as inflammatory bowel disease (IBD), ulcerative colitis, Crohn's disease, sprue, autoimmune arthritis, rheumatoid arthritis, Type I diabetes, multiple sclerosis, graft vs. host disease following bone marrow transplantation, osteoarthritis, juvenile chronic arthritis, Lyme arthritis, psoriatic arthritis, reactive arthritis, spondyloarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlejn purpurea, microscopic vasculitis of the kidneys, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, chlamydia, yersinia and salmonella associated arthropathy, spondyloarhopathy, atheromatous disease/arteriosclerosis, allergic colitis, atopic allergy, food allergies such as peanut allergy, tree nut allergy, egg allergy, milk allergy, soy allergy, wheat allergy, seafood allergy, shellfish allergy, or sesame seed allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, Acquired Immunodeficiency Disease Syndrome, Acquired Immunodeficiency Related Diseases, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, multiple sclerosis (all subtypes), insulin dependent diabetes mellitus, sympathetic ophthalmia, pulmonary hypertension secondary to connective tissue disease, Goodpasture's syndrome, pulmonary manifestation of polyarteritis nodosa, acute rheumatoid fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis (pollen allergies), anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, and eosinophilic gastroenteritis, and diarrhea.

In one embodiment, the invention provides methods for the treatment or prevention of at least one disease or disorder in a subject, comprising administering to the subject at least one composition comprising a SCFA or a compound comprising a SCFA moiety, optionally in combination with at least one additional agent or therapy.

In some embodiments, the administered compositions of the present invention can increase the number of disease-free days, reduce the severity of a disease or disorder, reduce the risk of developing a disease or disorder, reduce the risk of recurrence of a disease or disorder, or a combination thereof in the subject. The administered compositions of the present invention can increase the number of disease-free days by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment. The administered compositions of the present invention can reduce the severity of a disease or disorder by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment. The administered compositions of the present invention can reduce the risk of developing a disease or disorder by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment. The administered compositions of the present invention can reduce the risk of recurrence of a disease or disorder by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more in the subject as compared to a subject who is not receiving treatment.

In some embodiments, diseases and disorders that can be treated, prevented or ameliorated include, but are not limited to, inflammatory diseases and various cancer diseases. In some embodiments, the inflammatory diseases and disorders that can be treated or ameliorated include, but are not limited to, asthma, arthritis, allergic rhinitis, psoriasis, atopic dermatitis, inflammatory bowel diseases, Crohn's disease, an allergic or autoimmune disease or disorder associated with C-section delivery of a neonate, uveitis, and vasculitis. In some embodiments, the cancer diseases and disorders that can be treated or ameliorated include, but are not limited to, leukemias and lymphomas.

Methods for treating exemplary diseases and disorders are provided below.

Skin Disorders

The present invention is partly based upon the discovery that SCFAs are effective in the treatment of a skin disorder. In one embodiment, a combination of at least one SCFA with at least one other skin disorder treatment can be effective as a therapeutic approach for the treatment of a skin disorder.

In one embodiment, the present invention provides methods for treatment, inhibition, prevention, or reduction of a skin disease or disorder by administering a composition comprising a SCFA, as disclosed herein, to a subject in need thereof, optionally in combination with at least one additional agent or therapy. Skin diseases and disorders that may be treated using the methods of the invention include, but are not limited to: psoriasis, plaque psoriasis, guttate psoriasis, inverse psoriasis, pustular psoriasis, psoriasis vulgaris, seborrheic psoriasis, erythrodermic psoriasis, nail psoriasis, psoriatic arthritis, systemic lupus erythematosus (SLE) rash, scleroderma (systemic sclerosis), diabetes related skin conditions, rheumatoid arthritis and associated skin rashes (rheumatoid vasculitis), melanoma, vitiligo, eczema (atopic dermatitis), dyshidrotic eczema, rosacea, hives, impetigo, cellulitis, contact dermatitis, canker sores, acne, Lichen planus, actinic keratosis, ichthyosis vulgaris, dermatomyositis, and pemphigoid. In one embodiment, the present invention provides methods for treatment, inhibition, prevention, or reduction of a skin disease or disorder, comprising administering a composition comprising a SCFA, as disclosed herein, to a subject in need thereof.

In one embodiment, a subject suffering from a skin disorder is a human. In one embodiment, a subject suffering from a skin disorder is a non-human animal.

In one embodiment, the invention relates to compositions comprising at least one SCFA and at least one second compound for use as a therapeutic for the treatment of skin disorders. In one embodiment, the SCFA comprises one or more of formic acid, acetic acid, propionic acid, isobutyric acid, butyric acid, tributyrin, N-acetylbutyrate (as well as other forms of butyrate), isovaleric acid, valeric acid, isocaproic acid, caproic acid, lactic acid, succinic acid, pyruvic acid, octanoic acid, and dodecanoic acid. In one embodiment, the second compound comprises one or more of a PDE4 inhibitor, an anti-inflammatory compound, a disease-modifying antirheumatic drug (DMARD), an immunosuppressant, a biologic agent, and a Cox-2 inhibitor.

In one embodiment, a composition for use in methods of treating skin disorders comprises 900 mg butyrate, 100 mg propionate, 10 mg apremilast, 10 mg magnesium, and 50 IU vitamin D3.

In one embodiment, an exemplary method for the treatment of vasculitis comprises administration of a daily oral dose of at least 100 mg, at least 200 mg, at least 300 mg, at least 400 mg, at least 500 mg, at least 600 mg, at least 700 mg, at least 800 mg, at least 900 mg, at least 1 g, at least 2 g, at least 3 g, at least 4 g, at least 5 g, at least 6 g or more than 6 g of at least one SCFA, at least 1 time daily, at least 2 times daily, at least 3 times daily or more than 3 times daily, for at least one week, at least two weeks, at least three weeks, at least one month, at least 2 months, at least 3 months, at least 4 months, at least 5 months, at least 6 months or for more than 6 months.

In one embodiment, an exemplary daily oral dosage for use in methods of treating skin disorders comprises 3600 mg of butyrate, 400 mg propionate, 40 mg Magnesium, and 200 IU Vitamin D3. In one embodiment, an exemplary dosage for use in methods of treating skin disorders comprises 900-1800 mg of butyrate, 100-200 mg propionate, 10-20 mg Magnesium, and 50-100 IU Vitamin D3 administered 1-4 times daily. In one embodiment, the composition is administered 1-4 times daily for at least 1 week, at least 2 weeks, at least 3 weeks or for more than 3 week.

In one embodiment, an exemplary dosage for use in methods of treating skin disorders comprises 1-2 g of butyrate, 100 mg propionate, 10-15 mg Otezla, 10-20 mg Magnesium, and 80-100 IU Vitamin D3.

In one embodiment, the composition comprising at least one SCFA is an enteric coated, extended release and sustained release capsule.

In one embodiment, a method of treating skin disorders comprises administration of an oral formulation of a SCFA in combination with a topical ointment. An exemplary topical ointment for use in treating skin disorder may comprise 40% clobetazol (0.05%) cream, 20% calcipotriene (vit D, 0.005%) cream, 20% vit E (0.5%) cream and 20% salicylic acid (10%) cream. An alternative exemplary topical ointment for use in treating skin disorder may comprise 40% clobetazol (0.05%) cream, 20% calcipotriene (vit D, 0.005%) cream, 20% vit E (0.5%) cream and 20% zinc cream. In one embodiment zinc could be used together with salicylic acid in a topical ointment.

Eye Disease

In one embodiment, the invention relates to compositions comprising SCFA for use as therapeutics for the treatment of eye diseases or disorders. In one embodiment, the eye disease or disorder is inflammatory. In one embodiment, the inflammatory eye disease or disorder is uveitis. In one embodiment, a composition comprises one or more SCFAs. In one embodiment, the SCFAs include, but are not limited to, at least one of formic acid, acetic acid, propionic acid, isobutyric acid, butyric acid, tributyrin, N-acetylbutyrate (as well as other forms of butyrate), isovaleric acid, valeric acid, isocaproic acid, caproic acid, lactic acid, succinic acid, pyruvic acid, octanoic acid, and dodecanoic acid. In one embodiment, a composition comprises one or more of magnesium and calcium salts of one or more of the compounds disclosed herein.

In one embodiment, the invention comprises a formulated composition comprising a SCFA or a compound comprising a SCFA moiety. In one embodiment, the composition comprises an oral pharmaceutical or dietary composition comprising a SCFA or a compound comprising a SCFA moiety.

In one embodiment, the invention relates to a method of treating an eye disease or disorder comprising administering to a subject a composition comprising a SCFA. In one embodiment, the eye disease or disorder is inflammatory. In one embodiment, the inflammatory eye disorder is uveitis. In one embodiment, the composition is administered orally. In one embodiment, the composition is administered topically (e.g., in a cream). In one embodiment, a subject suffering from an eye disorder is a human. In one embodiment, a subject suffering from an eye disorder is a non-human animal.

In one embodiment, the present invention provides methods for treatment, inhibition, prevention, or reduction of an eye disease or disorder by administering a composition comprising a SCFA, as disclosed herein, to a subject in need thereof, optionally in combination with at least one additional agent or therapy. Eye diseases and disorders that may be treated using the methods of the invention include, but are not limited to uveitis, macular degeneration, age related macular degeneration (AMD), inflammation following a surgical procedure (e.g., a cataract surgery), Behçet's Disease of the eye, Sjogren's syndrome associated diseases or disorders (e.g., dry eyes), blepharitis associated diseases or disorders (e.g., rosacea) and any eye diseases or disorders associated with other diseases discussed in detail elsewhere herein. In one embodiment, the present invention provides methods for treatment, inhibition, prevention, or reduction of a disease associated with an eye disease or disorder, comprising administering a composition comprising a SCFA or a compound comprising a SCFA moiety, as disclosed herein, to a subject in need thereof. The present invention is partly based on the discovery that SCFA can be effective as a therapeutic approach for the treatment of an eye disease or disorder, including inflammatory eye diseases or disorders.

In one embodiment, an exemplary method for the treatment or prevention of eye diseases or disorders comprises administration of a daily oral dose of a composition comprising at least 100 mg, at least 200 mg, at least 300 mg, at least 400 mg, at least 500 mg, at least 600 mg, at least 700 mg, at least 800 mg, at least 900 mg, at least 1 g, at least 2 g, at least 3 g, least 4 g, at least 5 g, at least 6 g or more than 6 g of at least one SCFA at least 1 time daily, at least 2 times daily, at least 3 times daily or more than 3 times daily, for at least one week, at least two weeks, at least one month, at least 2 months, at least 3 months, at least 4 months, at least 5 months, at least 6 months or for more than 6 months.

In one embodiment, the composition comprising at least one SCFA is an enteric coated, extended release capsule. In one embodiment, an exemplary daily oral dose is 4-5 g of butyrate and 1.5-2 g of propionate in enteric coated, extended release capsules, twice/day.

In one embodiment, an exemplary method for the treatment or prevention of eye diseases or disorder comprises administration of a daily topical dose of a composition comprising at least 100 nM, at least 200 nM, at least 300 nM, at least 400 nM, at least 500 nM, at least 600 nM, at least 700 nM, at least 800 nM, at least 900 nM, at least 1 µM, at least 2 µM, at least 3 µM, least 4 µM, at least 5 µM, at least 6 µM, at least 7 µM, at least 8 µM, at least 9 µM, at least 10 µM, at least 15 µM, at least 20 µM, at least 25 µM, at least 30 µM, at least 35 µM, at least 40 µM, at least 45 µM, at least 50 µM, or more than 50 µM of at least one SCFA at least 1 time daily, at least 2 times daily, at least 3 times daily or more than 3 times daily, for at least one week, at least two weeks, at least three weeks, at least one month, at least 2 months, at least 3 months, at least 4 months, at least 5 months, at least 6 months or for more than 6 months.

In one embodiment, the composition comprising at least one SCFA is an eyedrop formulation. In one embodiment, an exemplary eyedrop formulation containing 20-30 µM of butyrate and 10-20 µM propionate can be administered at least twice/day in combination with lubricants.

In one embodiment, eyedrops should be given four times/day (in case of disease flares), and twice/day up to few months, in combination with oral doses of SCFAs.

In one embodiment, the method for the treatment or prevention of eye diseases or disorder includes administering a combination of SCFAs and antibiotics and/or steroids. For example, in case of infectious uveitis: during first 3-5 days, use eyedrops (or eye injection) with antibiotics/steroids (at the doses prescribed by doctors), then during following 2-3 weeks, use eyedrops containing a mixture of SCFAs (20-30 µM) and antibiotics/steroids (at half of the prescribed doses), then continue eyedrops with SCFAs (20-30 µM) only.

In one embodiment, the method for the treatment or prevention of eye diseases or disorder includes administering a combination of compositions comprising at least one SCFA. For example, in one embodiment, the method includes a combination of at least one SCFA formulated for oral administration and at least one SCFA formulated for use as eyedrops.

Allergy, Autoimmune and Asthma

The present invention contemplates the treatment or prevention of allergies, autoimmune disease and asthma. The present invention is partly based upon the discovery that SCFA are effective as a therapeutic approach for the treatment and prevention of an allergic, autoimmune and/or asthma disease or disorder.

In one embodiment, an autoimmune and/or allergic disease or disorder is at least one of Addison's disease, Agammaglobulinemia, Allergic rhinitis, Alopecia areata, Amyloidosis, Ankylosing spondylitis, Anti-GBM/Anti-TBM nephritis, Antiphospholipid syndrome (APS), Asthma, Autoimmune inner ear disease (AIED), Axonal & neuronal neuropathy (AMAN), Behcet's disease, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid/benign mucosal pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Food allergies, Gastroenteritis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammalglobulinemia, IgA Nephropathy, IgG4-related sclerosing disease, Inclusion body myositis (IBM), Inflammatory bowel disease, Interstitial cystitis (IC), Juvenile arthritis, Juvenile rheumatoid arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis (MS), Myasthenia gravis, Myositis, Narcolepsy, Neuromyelitis optica, Neutropenia, Ocular cicatricial pemphigoid, Optic neuritis, Palindromic rheumatism (PR), PANDAS (Pediatric Autoimmune Neuropsychiatric Disorders Associated, with, *Streptococcus*), Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome (polyneuropathy, organomegaly, endocrinopathy, monoclonal, gammopathy, skin changes), Polyarteritis nodosa, Polymyalgia rheumatica, Polymyositis, Postmyocardial infarction syndrome, Postpericardiotomy syndrome, Progesterone dermatitis, Psoriasis, Plaque psoriasis, Guttate psoriasis, Inverse psoriasis, Pustular psoriasis, Psoriasis Vulgaris, Seborrheic Psoriasis, Erythrodermic psoriasis, Nail psoriasis, Psoriatic arthritis, Pure red cell aplasia (PRCA), Pyoderma gangrenosum, Raynaud's phenomenon, Reactive Arthritis, Reflex sympathetic dystrophy, Reiter's syndrome, Relapsing polychondritis, Restless legs syndrome (RLS), Retroperitoneal fibrosis, Rheumatic fever, Rheumatoid arthritis (RA), Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Wegener's granulomatosis (Granulomatosis with Polyangiitis (GPA)).

In one embodiment, an allergic disease includes but is not limited to hay fever, food allergies, atopic dermatitis, allergic asthma, anaphylaxis, and the likes. Symptoms may include red eyes, an itchy rash, runny nose, shortness of breath, or inflammation. Exemplary allergic diseases include, but are not limited to, Food allergies (e.g., milk, soy, eggs, wheat, peanuts, tree nuts, fish, and shellfish), Latex allergies, Allergic rhinitis, Asthma, Atopic eczema, Anaphylaxis, Insect venom, Drug allergies, and any combination thereof. The prevalence of allergic diseases has increased all over the world during the last two decades.

In one embodiment the invention is useful for the prevention of an autoimmune and/or allergic disease or disorder in a C-section delivered neonate. Accordingly, the invention in one aspect encompasses administration of SCFA to a subject, including expecting mothers, mothers, and neonates, as an effective way in reducing the risk of developing an autoimmune and/or allergic disease or disorder in neonates, and may also be effective in treating an autoimmune and/or allergic disease or disorder in neonates.

In one embodiment, the invention relates to compositions comprising SCFAs for use as therapeutics for the treatment and prevention of an autoimmune and/or allergic disease or disorder in a C-section delivered neonate. In one embodiment, the composition comprises one or more SCFAs. In one embodiment, the composition comprises one or more salts of one or more SCFAs. In one embodiment, the composition comprises one or more biologically active derivatives of one or more SCFAs. In one embodiment, the composition comprises one or more precursors of one or more SCFAs. In one embodiment, a composition comprises one or more combinations of SCFAs, salts thereof, biologically active derivatives thereof, or precursors thereof. In one embodiment, a composition comprises one or more combinations of SCFAs, salts thereof, biologically active derivatives thereof, or precursors thereof, in combination with at least one other compound. In one embodiment, a composition comprises one or more of formic acid, acetic acid, propionic acid, isobutyric acid, butyric acid, tributyrin, N-acetylbutyrate (as well as other forms of butyrate), isovaleric acid, valeric acid, isocaproic acid, caproic acid, lactic acid, succinic acid, pyruvic acid, octanoic acid, and dodecanoic acid. In one embodiment, the composition is in the form of a capsule (enteric coated, time release) that can be used by women during late pregnancy. In another embodiment, the composition is in the form of a buffered solution of SCFAs that can be added to infant formula, pumped breast milk, baby food, and the like.

In one embodiment, the invention relates to a method of treating or preventing an autoimmune and/or allergic disease or disorder in a C-section delivered neonate comprising administering a composition comprising a SCFA to one or more subjects. In one embodiment, the administering a composition step occurs before birth of the neonate, wherein the composition is administered to the expectant mother. In one embodiment, the expectant mother is near term (about month 8 or 9 of pregnancy). In one embodiment, the SCFAs are given to the expectant mother orally for a time period of less than or equal to two months. In one embodiment, the SCFAs are administered to the expectant mother in the dose of 6 tablets per day for one week, followed by 3 tablets per day until the C-section is performed. In one embodiment, the dose of a single tablet is 600 mg of one or more SCFAs or salts thereof. In one embodiment, salts of one or more SCFAs are used, wherein the salts are sodium, magnesium, and/or calcium salts of one or more SCFAs. In one embodiment, the administering a composition step occurs after birth of the neonate, wherein the composition is administered to the mother, the neonate, or both the mother and the neonate. In one embodiment, the SCFAs are administered to the neonate, in the form of a mixture with food or drink. In one embodiment, the SCFAs are administered to the neonate, in the form of a supplement to baby formula or food for at least the first 18-24 months of life.

In one embodiment, the present invention provides methods for treatment, inhibition, prevention, or reduction of an autoimmune and/or allergic disease or disorder associated with C-section delivery of a neonate, by administering a composition comprising a SCFA or a compound comprising a SCFA moiety, as disclosed herein, to a subject in need thereof, optionally in combination with at least one additional agent or therapy. In one embodiment, the subject is the expectant mother. In one embodiment, the subject is the fetus. In one embodiment, the subject is the mother. In one embodiment, the subject is the neonate. Autoimmune and/or allergic diseases or disorders that may be treated using the methods of the invention include, but are not limited to any autoimmune and/or allergic disease or disorder described elsewhere herein. In one embodiment, the present invention provides methods for treatment, inhibition, prevention, or reduction of a disease associated with an autoimmune and/or allergic disease or disorder, comprising administering a composition comprising a SCFA or a compound comprising a SCFA moiety, as disclosed herein, to a subject in need thereof.

In one embodiment, a subject at risk of developing, or having already developed, an autoimmune or allergic disease or disorder is a human. In one embodiment, a subject is a non-human animal.

In one embodiment, an exemplary method for the treatment or prevention of autoimmune and/or allergic diseases or disorder comprises administration of a daily oral dose of a composition comprising at least 10 mg, at least 20 mg, at least 30 mg, at least 40 mg, at least 50 mg, at least 60 mg, at least 70 mg, at least 80 mg, at least 90 mg, at least 100 mg, at least 200 mg, at least 300 mg, at least 400 mg, at least 500 mg, at least 600 mg, at least 700 mg, at least 800 mg, at least 900 mg, at least 1 g, at least 2 g, at least 3 g, at least 4 g, at least 5 g, at least 6 g or more than 6 g of at least one SCFA at least 1 time daily, at least 2 times daily, at least 3 times daily or more than 3 times daily, for at least one week, at least two weeks, at least three weeks, at least one month, at least 2 months, at least 3 months, at least 4 months, at least 5 months, at least 6 months or for more than 6 months.

In one embodiment, the composition comprising at least one SCFA is an enteric coated, extended release capsule.

In one embodiment, the composition may be administered, for example, to a breastfeeding mother of a C-section delivered neonate. In such an embodiment, an exemplary daily oral dose for healthy mothers is 1-2 g of butyrate and 0.5-1 g of propionate and acetate in enteric coated, extended release capsules, 3 times/day during first month, then half of that dose (e.g., 0.5-1 g of butyrate and 0.25-0.5 g of propionate and acetate) for at least 1, at least 2, at least 3 or more than 3 additional months.

In one embodiment, the composition may be administered, for example, to a C-section delivered neonate. In such an embodiment, an exemplary daily oral dose may be at least 10 mg, at least 20 mg, at least 30 mg, at least 40 mg, at least 50 mg, at least 60 mg, at least 70 mg, at least 80 mg, at least 90 mg, 100 mg, at least 200 mg, at least 300 mg, at least 400 mg, at least 500 mg, at least 600 mg, at least 700 mg, at least 800 mg, at least 900 mg, or more than 1 g of at least one SCFA at least 1 time daily, at least 2 times daily, at least 3 times daily, at least 4 times daily, at least 5 times daily, at least 6 times daily, at least 7 times daily or more than 7 times daily. Such an embodiment may be formulated, for example as an additive to a nutritional formula, such as an infant food formula, for administration to a C-section delivered neonate. In such an embodiment, an exemplary daily oral dose for administration to a C-section delivered neonate comprises 80-100 mg of butyrate, 20-30 mg of acetate and propionate during the first month following delivery, followed by 100-120 mg of butyrate and 30-40 mg of acetate and propionate for the subsequent 3-5 months.

Vasculitis

In one embodiment, the present invention provides methods for treatment, inhibition, prevention, or reduction of a vasculitis disease or disorder by administering a composition comprising a SCFA or a compound comprising a SCFA moiety, as disclosed herein, to a subject in need thereof, optionally in combination with at least one additional agent or therapy. Vasculitis diseases and disorders that may be treated using the methods of the invention include, but are not limited to, lymphangitis, polymyalgia rheumatica, Takayasu's arteritis, temporal arteritis, Buerger's disease, Kawasaki disease, polyarteritis nodosa, Behçet's syndrome, eosinophilic granulomatosis with polyangiitis, cutaneous vasculitis, Henoch-Schönlein purpura, microscopic polyannulomatosis, cutaneous small-vessel vasculitis, granulomatosis with polyangiitis, Behçet's disease, and giant cell arteritis. In one embodiment, the present invention provides methods for treatment, inhibition, prevention, or reduction of a disease associated with vasculitis, comprising administering a composition comprising a SCFA or a compound comprising a SCFA moiety, as disclosed herein, to a subject in need thereof.

In various embodiments, one or more SCFA or compound comprising a SCFA moiety may be used in combination with one or more corticosteroid drugs, such as prednisone or methylprednisolone (Medrol) for the treatment of vasculitis. In other embodiments, one or more SCFA or compound comprising a SCFA moiety may be used in combination with one or more cytotoxic or immunosuppressant drugs, which decrease the function of immune system cells causing the inflammation. They include azathioprine (Azasan, Imuran), methotrexate (Trexall, Rheumatrex) and cyclophosphamide. In other embodiments, one or more SCFA or compound comprising a SCFA moiety may be used in combination with Rituximab (Rituxan), for treating some types of vasculitis.

In one embodiment, an exemplary method for the treatment of vasculitis comprises administration of a daily oral dose of at least 100 mg, at least 200 mg, at least 300 mg, at least 400 mg, at least 500 mg, at least 600 mg, at least 700 mg, at least 800 mg, at least 900 mg, at least 1 g, at least 2 g, at least 3 g, at least 4 g, at least 5 g, at least 6 g or more than 6 g of at least one SCFA, at least 1 time daily, at least 2 times daily, at least 3 times daily or more than 3 times daily, for at least one week, at least two weeks, at least three weeks, at least one month, at least 2 months, at least 3 months, at least 4 months, at least 5 months, at least 6 months or for more than 6 months.

In one embodiment, the composition comprising at least one SCFA is an enteric coated, extended release capsule.

In one embodiment, an exemplary method for the treatment of vasculitis comprises administration of a daily oral dose of 5 g-6 g of butyrate in enteric coated, extended release capsules, at least 3 times daily for one month, followed administration of a daily oral dose of 3 g-4 g of butyrate in enteric coated, extended release capsules, at least 2 times daily for at least 2 months. In one embodiment, higher doses can be used for the treatment of disease flares, including, but not limited to, stress triggered disease flares.

In one embodiment, the method includes administering a composition comprising a SCFA in combination with other steroids and/or chemotherapeutic agents. In such an embodiment, the dosage level of the other steroids and/or chemotherapeutic agents may be reduced relative to the recommended or administered dosage for a subject undergoing treatment with the steroids and/or chemotherapeutic agents alone.

Lymphoma

In one embodiment, the present invention provides methods for treatment, inhibition, prevention, or reduction of a lymphoma disease or disorder by administering a composition comprising a SCFA or a compound comprising a SCFA moiety, as disclosed herein, to a subject in need thereof, optionally in combination with at least one additional agent or therapy. Lymphoma diseases and disorders that may be treated using the methods of the invention include, but are not limited to activated B-cell-like diffuse large B cell lymphoma (ABC DLBCL), follicular lymphoma (FL), mucosa associated lymphoid tissue lymphoma (MALT), Hodgkin lymphoma (HL), and primary mediastinal B cell lymphoma (PMBL). In one embodiment, the present invention provides methods for treatment, inhibition, prevention, or reduction of a disease associated with lymphoma, or prevention of tumor relapse, comprising administering a composition comprising a SCFA or a compound comprising a SCFA moiety, as disclosed herein, to a subject in need thereof.

In various embodiments, one or more SCFA or compound comprising a SCFA moiety may be used in combination with one or more other lymphoma treatment therapies. In various embodiments, the one or more other lymphoma treatment therapies includes radiation therapy, and/or rituximab (anti-CD20 antibody). In various embodiments, a composition of the invention is administered before, during, or after another treatment for lymphoma. In various embodiments, another treatment for lymphoma includes one or more chemotherapeutic agents, anti-proliferative agents, anti-tumor agents, antineoplastic agents, anti-angiogenic agents, and/or other anti-cancer agents as disclosed elsewhere herein.

In one embodiment, the method includes administering a composition comprising a SCFA in combination with other anti-lymphoma or anti-tumor agents, including chemotherapeutic agents, cytotoxic/anti-neoplastic agents and anti-angiogenic agents. In such an embodiment, the dosage level of the other anti-lymphoma or anti-tumor agents may be reduced relative to the recommended or administered dosage for a subject undergoing treatment with the other anti-lymphoma or anti-tumor agents alone.

Leukemia

In one embodiment, the present invention provides methods for treatment, inhibition, prevention, or reduction of a leukemia disease or disorder by administering a composition comprising a SCFA or a compound comprising a SCFA moiety, as disclosed herein, to a subject in need thereof, optionally in combination with at least one additional agent or therapy. Leukemia diseases and disorders that may be treated using the methods of the invention include, but are not limited to myeloproliferative neoplasm (MPN), polycythemia vera (PV), essential thrombocytosis (ET), idiopathic/myelofibrosis (Mf), acute myeloid leukemia (AML), childhood acute lymphoblastic leukemia (ALL), and blood cancer. In one embodiment, the present invention provides methods for treatment, inhibition, prevention, or reduction of a disease associated with leukemia, for treating or preventing relapse, or for prevention of primary tumor onset, of at least one type of leukemia, or for preventing the evolution of MPN to leukemia comprising administering a composition comprising a SCFA or a compound comprising a SCFA moiety, as disclosed herein, to a subject in need thereof. In one embodiment, the at least one SCFA or compound comprising a SCFA moiety is administered before, during, or after the administration of at least one additional agent or therapy for the treatment or prevention of leukemia. In a particular embodiment, a composition of the invention is administered after a therapeutic phase as part of a strategy to prevent relapse, or for prevention of primary tumor onset, of the leukemia. In various embodiments, a composition of the invention is administered before, during, or after another treatment for leukemia. In various embodiments, another treatment for leukemia includes one or more chemotherapeutic agents, antiproliferative agents, anti-tumor agents, antineoplastic agents, antiangiogenic agents, and/or other anti-cancer agents as disclosed elsewhere herein.

In one embodiment, treatment comprises two phases. The first phase, referred to as induction, may include chemotherapy, for example, treatment with arabinosylcytosine (ara-C) and daunomycin, optionally combined with, cladribine (Leustatin, 2-CdA). Induction is considered successful if remission is achieved. The second phase, referred to as consolidation, includes long term high dose ara-C. Alternatively, allogeneic or autologous stem cell transplant may be used. In one embodiment, a SCFA therapeutic compound of the invention is administered to the subject before, during, and/or after induction. In another embodiment, a SCFA therapeutic compound of the invention is administered to the subject before, during, and/or after consolidation. In one embodiment, a SCFA therapeutic compound of the invention is administered to the subject before, during, and/or after induction and before, during, and/or after consolidation.

In various embodiments, a composition of the invention is administered as part of a method to treat or prevent relapse, or for prevention of primary tumor onset, of at least one leukemia. In one embodiment, the at least one leukemia depends upon constitutive activation of JAK/STAT signaling. In one embodiment, the at least one leukemia is BCR/ABL negative. In one embodiment, the treatment method delays or prevents leukemia recurrence or relapse, or for prevention of primary tumor onset. In one embodiment, the treatment method decreases the toxicity profiles of standard of care treatments started at the time of diagnosis, thereby increasing long term quality of life.

In one embodiment, the method includes administering a composition comprising a SCFA in combination with other anti-leukemia or anti-tumor agents, including chemotherapeutic agents, cytotoxic/anti-neoplastic agents and anti-angiogenic agents. In such an embodiment, the dosage level of the other anti-leukemia or anti-tumor agents may be reduced relative to the recommended or administered dosage for a subject undergoing treatment with the other anti-leukemia or anti-tumor agents alone.

Immunotherapy

In one embodiment, the invention provides a method for stimulating, eliciting or enhancing an immune response in a subject individual (individual) comprising administering to a subject an immunotherapeutic agent in combination with a composition comprising a SCFA or a compound comprising a SCFA moiety. In one embodiment, the subject may be at risk for having a disease, be diagnosed as having a disease, have previously been treated for a disease, or be contemporaneously be treated for the disease using a treatment method (e.g., a treatment method that does not include the use of a composition of the invention described herein).

The present invention is partly based upon the discovery that administration of at least one short chain fatty acid (SCFA) can be effective as a therapeutic approach for the treatment or prevention of an adverse effect associated with immunotherapy of cancer. It is expected that the therapeutic effect of treatments using compositions comprising at least one SCFA will not interfere significantly with the benefits of the immunotherapy, but will treat or prevent undesired adverse effects associated with immunotherapy of cancer. Therefore, in one embodiment, the invention relates to compositions comprising at least one SCFA for use as a therapeutic for the treatment or prevention of adverse effects associated with immunotherapy of cancer.

In one embodiment, the present invention provides methods for treatment, inhibition, prevention, or reduction of an adverse effect associated with cancer immunotherapy by administering a composition comprising a SCFA or a compound comprising a SCFA moiety, as disclosed herein, to a subject in need thereof, optionally in combination with at least one additional agent or therapy. Adverse effects associated with cancer immunotherapy that may be treated using the methods of the invention include, but are not limited to cytokine release syndrome (CRS), neurological toxicity, on-target/off-tumor recognition, anaphylaxis, graft versus host disease (GVHD), off-target antigen recognition, and macrophage activation syndrome (MAS). In one embodiment, the present invention provides methods for treatment, inhibition, prevention, or reduction of a disease associated with an adverse effect associated with cancer immunotherapy, comprising administering a composition comprising at least one SCFA or compound comprising a SCFA moiety, as disclosed herein, to a subject in need thereof. In one embodiment, the adverse effect includes a combination of adverse effects.

In one embodiment, a subject suffering from adverse effects associated with immunotherapy of cancer is a human. In one embodiment, a subject suffering from adverse effects associated with immunotherapy of cancer is a non-human animal.

In one embodiment, to stimulate an immune response, the subject individual is administered (i) at least one SCFA or compound comprising a SCFA moiety, and (ii) at least one immunotherapeutic agent. Typically, the administration of at least one SCFA or compound comprising a SCFA moiety and the immunotherapeutic agent will be in the form of a vaccine or administered in a vaccine regimen. The at least one SCFA or compound comprising a SCFA moiety and the immunotherapeutic agent can be administered at about the same time to the subject individual, or can be administered separately and/or sequentially.

Immunotherapeutic agents that may be administered according to the methods of the invention include, but are not limited to, one or more cancer antigens, one or more antigens derived from a virus associated with cancer, and an anti-cancer antibody.

A cancer antigen may be (a) a cell surface antigen that can be found on a malignant cell, (b) an antigen that can be found inside a malignant cell or (c) a mediator of tumor cell growth. The term "cancer antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

The cancer antigen can be a cell, a protein, a peptide, a fusion protein, DNA encoding a peptide or protein, RNA encoding a peptide or protein, a glycoprotein, a lipoprotein, a phosphoprotein, a carbohydrate, a lipopolysaccharide, a lipid, a chemically linked combination of two or more thereof, a fusion or two or more thereof, or a mixture of two or more thereof. In another embodiment, the cancer antigen is a peptide comprising about 6 to about 24 amino acids; from about 8 to about 20 amino acids; from about 8 to about 12 amino acids; from about 10 to about 10 amino acids; or from about 12 to about 20 amino acids. In one embodiment, the cancer antigen is a peptide having a MEW Class I binding motif or a MHC Class II binding motif. In another embodiment, the cancer antigen comprises a peptide that corresponds to one or more cytotoxic T lymphocyte (CTL) epitopes.

In one embodiment, the present invention provides methods for treatment, inhibition, prevention, or reduction of an adverse effect associated with cancer immunotherapy by administering a composition comprising a SCFA or a compound comprising a SCFA moiety, as disclosed herein, to a subject in need thereof, optionally in combination with at least one immunotherapeutic agent.

In one embodiment, the immunotherapy is chimeric antigen receptor T-cell (CAR-T) therapy. In some embodiments, a composition of the invention is administered before, during, or after CAR-T therapy for the treatment of cancer, for the treatment or prevention of at least one adverse effect associated with CAR-T therapy. Particular adverse effects treatable and/or preventable by compositions of the present invention include, but are not limited to: cytokine release syndrome (CRS), neurological toxicity, on-target/off-tumor recognition, anaphylaxis, graft versus host disease (GVHD), off-target antigen recognition, and macrophage activation syndrome (MAS). Existing or developing treatment or prevention of these adverse effects include pharmacological immunosuppression (i.e., IL-6R blockade, systemic corticosteroids such as dexamethasone, monoclonal antibodies, lymphodepleting chemotherapy with agents such as cyclophosphamide), suicide genes or elimination genes (i.e., killing of CAR-T cells), and targeted activation (i.e., conditional activation of CAR-T cells with a drug or another agent). Therefore, in one embodiment, the treatment compositions of the present invention are combined with at least one other strategy to reduce, prevent, treat, or ameliorate one or more adverse effects associated with immunotherapy of cancer. In one embodiment, the invention provides a composition for treating or preventing the onset of an adverse effect associated with immunotherapy of cancer. In one embodiment, the composition comprises at least one SCFA or a compound comprising a SCFA moiety. In one embodiment, the immunotherapy comprises CAR-T therapy. In another embodiment, the immunotherapy comprises a therapy involving at least one other anti-cancer composition. In some embodiments, a composition of the invention is administered before, during, or after chemotherapy for the treatment of cancer.

In one embodiment, the composition comprising at least one SCFA is administered in parallel to chemotherapy: several days before CAR-T cell infusion (only SCFAs), and up to several weeks after CAR-T cell infusion (SCFAs in combination with chemotherapeutic agents at reduced levels relative to a subject undergoing chemotherapy alone).

In one embodiment, an exemplary daily oral dose for use in methods of immunotherapy is daily oral dose of at least 2 g, at least 3 g, at least 4 g, at least 5 g, at least 6 g or more than 6 g of at least one SCFA, at least 2 times daily, at least 3 times daily or more than 3 times daily, for at least one week, at least two weeks, at least three weeks, at least one month, at least 2 months, at least 3 months, at least 4 months, at least 5 months, at least 6 months or for more than 6 months.

In one embodiment, an exemplary daily oral dose for use in methods of immunotherapy is daily oral dose of 5-6 g of butyrate and 2-3 g of propionate. In one embodiment, the composition comprising at least one SCFA is an enteric coated, extended release capsule. In one embodiment, the composition is administered 3 times/day.

Combination with Additional Agents

The present invention is also directed to a method of treating or preventing a disease or disorder as described above in combination with one or more additional agents.

The combination can be in a single formulation or can be separate and administered in sequence (either a composition comprising at least one SCFA, or a molecule comprising a SCFA moiety, first and then a composition comprising an additional agent, or a composition comprising an additional agent first and then a composition comprising at least one SCFA, or a molecule comprising a SCFA moiety). In some embodiments, the at least one SCFA, or a molecule comprising a SCFA moiety, can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the composition comprising at least one additional agent is administered to the subject. In other embodiments, the composition comprising at least one additional agent can be administered to the subject about 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 0.25 hours, 0.5 hours, 0.75 hours, 1 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, 96 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 1 week, 2 weeks, 3 weeks, 4 weeks, 5 weeks, 6 weeks, 7 weeks, or 8 weeks before the composition comprising at least one SCFA, or a molecule comprising a SCFA moiety, is administered to the subject.

In one embodiment, the invention provides a general concept for administering at least one of these agents, or a biologically-active derivative thereof, in combination with at least one short chain fatty acid (SCFA), or a biologically-active derivative or precursor thereof, as a therapy for treating or preventing a disease or disorder in a subject in need thereof. In one embodiment, the composition of the invention comprises at least one of these agents, or a biologically-active derivative thereof, and at least one SCFA, or a biologically-active derivative or precursor thereof.

Exemplary therapeutic agents that can be included in a composition of the invention or administered in combination with the composition of the invention are provided.

Checkpoint Inhibitors

In one embodiment, the method comprises administering to a subject in need thereof a composition comprising at least one SCFA, or a biologically-active derivative or precursor thereof, in combination with one or more immune checkpoint inhibitor. "Checkpoint inhibitor" as used herein includes inhibitors or molecules that block immune checkpoints as commonly understood in the field of cancer immunotherapy. Commonly the checkpoint inhibitors are antibodies that block the immune checkpoint proteins. Immune checkpoint proteins include, but are not limited to, PD1, PDL1, PDL2, CTLA-4, LAG3, TIM3, B7-H3, BTLA, VISTA, CD40, CEACAM1, CD80, CD86, OX40, CD27, GITR, DNAM-1, TIGIT, TMIGD2 and DC-SIGN. Some examples of known checkpoint inhibitors include, but are not limited to, ipilimumab, pembrolizumab, nivolumab, pidilizumab, atezolizumab, avelumab, druvbalumab and others. In one embodiment, the composition as described above can comprise at least one SCFA, or a molecule comprising a SCFA moiety, in combination with an antibody to a checkpoint protein.

In one embodiment, the combination of the at least one SCFA, or a molecule comprising a SCFA moiety, and checkpoint inhibitor induces the immune system more efficiently than the checkpoint inhibitor alone. This more efficient immune response provides increased efficacy in the treatment and/or prevention of a particular disease or disorder.

In some embodiments, the immune response can be increased by about 0.5-fold to about 15-fold, about 0.5-fold to about 10-fold, or about 0.5-fold to about 8-fold. Alternatively, the immune response in the subject administered the combination of the at least one SCFA, or a molecule comprising a SCFA moiety, and checkpoint inhibitor can be increased by at least about 0.5-fold, at least about 1.0-fold, at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, or at least about 15.0-fold.

In still other alternative embodiments, the immune response in the subject administered the combination of the at least one SCFA, or a molecule comprising a SCFA moiety, and checkpoint inhibitor can be increased about 50% to about 1500%, about 50% to about 1000%, or about 50% to about 800%. In other embodiments, the immune response in the subject administered the combination of the at least one SCFA, or a molecule comprising a SCFA moiety, and checkpoint inhibitor can be increased by at least about 50%, at least about 100%, at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1050%, at least about 1100%, at least about 1150%, at least about 1200%, at least about 1250%, at least about 1300%, at least about 1350%, at least about 1450%, or at least about 1500%.

Anti-Inflammatory Agents

In one embodiment, the method comprises administering to a subject in need thereof a composition comprising at least one SCFA, or a biologically-active derivative or precursor thereof, in combination with one or more anti-inflammatory agent. Exemplary anti-inflammatory agents that can be used in combination with the compositions of the invention include, but are not limited to nonsteroidal anti-inflammatory drugs (NSAIDs) such as diclofenac (e.g., Arthrotec®), diflunisal (e.g., Dolobid®), etodolac (e.g., Lodine®), fenoprofen (e.g., Nalfon®), ibuprofen (e.g., Advil®, Motrin®, and others), indomethacin (e.g., Arthrexin®), ketoprofen (e.g., Oruvail®) ketorolac (e.g., Toradol®), fosfomycin tromethamine (e.g., Monural®), meclofenamate (e.g., Meclomen®), nabumetone (e.g., Relafen®), naproxen (e.g., Anaprox®, and others). Oxaprozin (e.g., Daypro®) piroxicam (e.g., Feldene®) sulindac (e.g., tolmetin (e.g., Tolectin®, and others), Flavenoids (e.g., luteolin, fisetin, and apigenin), steroids, antihistamines, Loratadine, Theophylline, Doxantrazole, Quercetin, 8-bromo cyclic AMP, Disodium cromoglicate, Beclomethasone dipropionate, Budesonide, Budesonide/Formoterol, Fluticasone, Fluticasone inhaled powder, Fluticasone/Salmeterol, Mometasone, Mometasone/formoterol, Cromolyn, Omalizumab, Inhaled short- or long-acting beta2-agonists, Leukotriene modifiers, and Theophylline. In one embodiment, the method comprises administering to a subject in need thereof a composition comprising at least one SCFA, or a biologically-active derivative or precursor thereof, and additionally one or more anti-inflammatory agent. In one embodiment, the method comprises administering to a subject in need thereof a composition comprising at least one SCFA, or a biologically-active derivative or precursor thereof, in combination with a composition comprising one or more anti-inflammatory agent.

PDE4 Inhibitors

In one embodiment, the method comprises administering to a subject in need thereof a composition comprising at least one SCFA, or a biologically-active derivative or precursor thereof, in combination with one or more phosphodiesterase 4 (PDE4) inhibitors. A non-limiting selection of PDE4 inhibitors is presented in U.S. Patent Application Publication No. 2002/0111495, which is incorporated herein by reference. In one embodiment, the method comprises administering to a subject in need thereof a composition comprising at least one SCFA, or a biologically-active derivative or precursor thereof, and additionally one or more PDE4 inhibitor. In one embodiment, the method comprises administering to a subject in need thereof a composition comprising at least one SCFA, or a biologically-active derivative or precursor thereof, in combination with a composition comprising one or more PDE4 inhibitor.

Disease-Modifying Antirheumatic Drugs (DMARD)

In one embodiment, the method comprises administering to a subject in need thereof a composition comprising at least one SCFA, or a biologically-active derivative or precursor thereof, in combination with one or more disease-modifying antirheumatic drugs (DMARD) or immunosuppressants may be included in the compositions of the invention. DMARDs are known in the art, and include, but are not limited to, methotrexate (Rheumatrex®), sulfasalazine (Azulfidine®), mycophenolate mofetil (CellCept®), and cyclosporine (Sandimmune®, or Neroal®). In one embodiment, the method comprises administering to a subject in need thereof a composition comprising at least one SCFA, or a biologically-active derivative or precursor thereof, and additionally one or more DMARD. In one embodiment, the method comprises administering to a subject in need thereof a composition comprising at least one SCFA, or a biologically-active derivative or precursor thereof, in combination with a composition comprising one or more DMARD.

Biologic Agents

In one embodiment, the method comprises administering to a subject in need thereof a composition comprising at least one SCFA, or a biologically-active derivative or precursor thereof, in combination with one or more biologic drugs. Exemplary biologic drugs contemplated by the present invention include, but are not limited to, etanercept (Enbrel®), infliximab (Remicade®), apremilast (Otezla®), and adalimumab (Humira®). In one embodiment, the method comprises administering to a subject in need thereof a composition comprising at least one SCFA, or a biologically-active derivative or precursor thereof, and additionally one or more biologic agent. In one embodiment, the method comprises administering to a subject in need thereof a composition comprising at least one SCFA, or a biologically-active derivative or precursor thereof, in combination with a composition comprising one or more biologic agent.

Cox-2 Inhibitors

In one embodiment, the method comprises administering to a subject in need thereof a composition comprising at least one SCFA, or a biologically-active derivative or precursor thereof, in combination with one or more Cox-2 inhibitors. Cox-2 inhibitors include, but are not limited to, celecoxib (Celebrex®), valdecoxib (Bextra®), and meloxicam (Mobic®). In one embodiment, the method comprises administering to a subject in need thereof a composition comprising at least one SCFA, or a biologically-active derivative or precursor thereof, and additionally one or more Cox-2 inhibitors. In one embodiment, the method comprises administering to a subject in need thereof a composition comprising at least one SCFA, or a biologically-active derivative or precursor thereof, in combination with a composition comprising one or more Cox-2 inhibitors.

Magnesium, Vitamin D3, and Vitamin E

In one embodiment, the method comprises administering to a subject in need thereof a composition comprising at least one SCFA, or a biologically-active derivative or precursor thereof, and additionally one or more of magnesium, vitamin D3, and vitamin E (d-α-tocopherol acetate). Magnesium is a co-factor for more than 300 enzymes that regulate diverse biochemical reactions including regulation of blood glucose levels, detoxification, and others. Vitamin D3 deficiency is frequent in patients with immune disorders. Vitamin E has distinctive antioxidant activities. In one embodiment, the method comprises administering to a subject in need thereof a composition comprising at least one SCFA, or a biologically-active derivative or precursor thereof, and additionally one or more of magnesium, vitamin D3, and vitamin E. In one embodiment, the method comprises administering to a subject in need thereof a composition comprising at least one SCFA, or a biologically-active derivative or precursor thereof, in combination with a composition comprising one or more of magnesium, vitamin D3, and vitamin E.

Other Agents

In one embodiment, the method comprises administering to a subject in need thereof a composition comprising at least one SCFA, or a biologically-active derivative or precursor thereof, and additionally one or more additional therapeutic agents. In one embodiment, the method comprises administering to a subject in need thereof a composition comprising at least one SCFA, or a biologically-active derivative or precursor thereof, in combination with a composition comprising one or more additional therapeutic agents. Additional therapeutic agents that are contemplated for administration according to the methods of the invention include, but are not limited to, rofecoxib, celecoxib, folic acid, sulfasalazine, naproxen, leflunomide, methylprednisolone acetate, parenteral gold, oral gold, indomethacin, hydroxychloroquine, hydroxychloroquine sulfate, sulindac, prednisone, betamethasone diprop augmented, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac, sodium/misoprostol, fluocinonide, glucosamine sulfate, gold sodium thiomalate, hydrocodone bitartrate/apap, risedronate sodium, sulfadiazine, thioguanine, valdecoxib, small molecule inhibitor of KDR (ABT-123), small molecule inhibitor of Tie-2, clobetasol propionate, triamcinolone acetonide, halobetasol propionate, tazarotene, fluocinonide, betamethasone diprop augmented, fluocinolone, acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, coal tar, diflorasone diacetate, folate, lactic acid, methoxsalen, methylprednisolone acetate, prednisone, sunscreen, salicylic acid, halcinonide, anthralin, clocortolone pivalate, coal extract, coal tar/salicylic acid, coal tar/salicylic acid/sulfur, desoximetasone, diazepam, emollient, pimecrolimus emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, alefacept, efalizumab, tacrolimus, pimecrolimus, PUVA, UVB, sulfasalazine, alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (Humira® Abbott Laboratories, a human anti-TNF mAb, described in U.S. Pat. No. 6,090,382 as D2E7). Additional TNF antibodies which can be used in the invention are described in U.S. Pat. Nos. 6,593,458; 6,498,237; 6,451,983; and 6,448,380, each of which is incorporated by reference herein, talampanel, teriflunomide, TGF-beta2, tiplimotide, VLA-4 antagonists (for example, TR-14035, VLA4 Ultrahaler, Antegran-ELAN/Biogen), interferon gamma antagonists, IL-4 agonists, humanized IL-6 antibody tocilizumab, steroids (e.g., dexamethasone, prednisone, prednisolone, triamcinolone acetonide, fluorometholone, and difluprednate), rapamycin, lampalizumab, fluocinolone acetatonide, macuCLEAR eyedrops, bone marrow CD34 stem cells, other stem cells, ranibizumab, brimonidine, LFG316, ORACEA®, emixustat hydrochloride, sirolimus, copaxone, othera eye drops, AL-78898A, and eculizumab.

Interleukin IL-17 Inhibitors

Interleukin IL-17 has been shown to stimulate TNFα production. Anti-IL-17 drugs include, but are not limited to brodalumab, ixekizumab and secukinumab. In one embodiment, the method comprises administering to a subject in need thereof a composition comprising at least one SCFA, or a biologically-active derivative or precursor thereof, and additionally one or more inhibitors of IL-17. In one embodiment, the method comprises administering to a subject in need thereof a composition comprising at least one SCFA, or a biologically-active derivative or precursor thereof, in combination with a composition comprising one or more inhibitors of IL-17.

IFN-γ Inhibitors

A key Th1-type cytokine involved in the pathogenesis of inflammatory disease is IFN-γ which inhibits apoptosis of keratinocytes by stimulating expression of the anti-apoptotic protein Bcl-x. This contributes to the progression of inflammatory disease. Therefore, in one embodiment, the method of the invention may comprise administration of the composition of the invention in combination with one or more inhibitors of IFN-γ. In one embodiment, an inhibitor of IFN-γ may be at least one of an anti-IFN-γ antibody, a soluble IFN-γ receptor, and a combination thereof. In one embodiment, the method comprises administering to a subject in need thereof a composition comprising at least one SCFA, or a biologically-active derivative or precursor thereof, and additionally one or more inhibitors of IFN-γ. In one embodiment, the method comprises administering to a subject in need thereof a composition comprising at least one SCFA, or a biologically-active derivative or precursor thereof, in combination with a composition comprising one or more inhibitors of IFN-γ.

VEGF Inhibitors

Vascular endothelial growth factor (VEGF) is implicated in the pathologic angiogenesis observed in inflammatory disease which is characterized by enhanced expression of VEGF (by epidermal keratinocytes) at mRNA and protein levels, and VEGF receptors (by tortuous microvessels in the upper dermis) (Man et al., 2008, J Cell Mol Med., 12(2): 649-60; Marina et al., 2015, Clujul Med, 88(3):247-52). Therefore, in one embodiment, the method of the invention may comprise administration of the composition of the invention in combination with at least one VEGF inhibitor. In one embodiment, the VEGF inhibitor is an antibody, for example, a monoclonal antibody. In one embodiment, the VEGF inhibitor is at least one of bevacizumab, sunitinib, sorafenib, pazopanib, brivanib alaninate, cediranib, vandetanib, motesanib, linifinib, axitinib, and aflibercept. In one embodiment, the method comprises administering to a subject in need thereof a composition comprising at least one SCFA, or a biologically-active derivative or precursor thereof, and additionally one or more VEGF inhibitor. In one embodiment, the method comprises administering to a subject in need thereof a composition comprising at least one SCFA, or a biologically-active derivative or precursor thereof, in combination with a composition comprising one or more VEGF inhibitor.

HDAC Inhibitors

Butyrate is one of the strongest histone deacetylase (HDAC) inhibitors. HDAC inhibition may stimulate differentiation of naïve T-cells into Treg cells, a subset of $T_{CD4}$ cells (expressing transcription factor FoxP3, which is crucial for Treg development). Treg cells are involved in the maintenance of self-tolerance by suppressing activation and expansion of self-reactive lymphocytes and thus have a critical role in preventing autoimmunity. Therefore, the present invention provides a number of compositions that could promote Tregs and/or cells and/or pathways associated with FoxP3, at least in part by HDAC inhibition. Therefore, in one embodiment, the composition of the invention comprises at least one compound that promotes the differentiation of naïve T-cells into Treg cells.

Therefore, in one embodiment, the method of the invention may comprise administration of the composition of the invention in combination with one or more HDAC inhibitor. Exemplary HDAC inhibitor include, but are not limited to, TSA, SAHA, CBHA, LAQ-824, PDX-101, LBH-589, ITF2357, PCI-24781, FK-228, valproic acid, phenyl butyrate, butyrate, AN-9, MS-275, and MGCD0103 (Dokmanovic, M. et al., 2007, 5(10):981-989). In one embodiment, the method comprises administering to a subject in need thereof a composition comprising at least one SCFA, or a biologically-active derivative or precursor thereof, and additionally one or more HDAC inhibitor. In one embodiment, the method comprises administering to a subject in need thereof a composition comprising at least one SCFA, or a biologically-active derivative or precursor thereof, in combination with a composition comprising one or more HDAC inhibitor.

AMPK Activators

Adenosine monophosphate kinase (AMPK) promotes expression of transcription factor FoxP3, which in turn stimulates Treg cell differentiation and function. In one embodiment, the method of the invention may comprise administration of the composition of the invention in combination with one or more natural AMPK activators, including but not limited to, rosehip (from *Rosa canina*) and jiaogulan extracts (from *Gynostemma pentaphyllum*) or other natural AMPK activators. Exemplary AMPK activators from natural products, are described in Uddin et al., 2013, Natural Product Sciences, 19(1):1-7, which is incorporated herein by reference.

IDO Inhibitors

In one embodiment, the method of the invention may comprise administration of the composition of the invention in combination with one or more IDO inhibitor. IDO inhibitors including, but not limited to, 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in WO 2004/094409, both the contents of which are incorporated in their entirety herein.

In one embodiment, the method comprises administering to a subject in need thereof a composition comprising at least one SCFA, or a biologically-active derivative or precursor thereof, and additionally one or more IDO inhibitor. In one embodiment, the method comprises administering to a subject in need thereof a composition comprising at least one SCFA, or a biologically-active derivative or precursor thereof, in combination with a composition comprising one or more IDO inhibitor.

Agents for the Treatment of Diabetes or Diabetes Related Conditions

In one embodiment, the method of the invention may comprise administration of the composition of the invention in combination with one or more agent for the treatment of diabetes or diabetes related conditions. The use of other agents (e.g., insulin) and diets (low sugar) can be used in combination with the SCFA or compound comprising a SCFA moiety of the present invention to increase therapeutic efficacy thereof. Anti-diabetes compounds that may be combined with the SCFA or compound comprising a SCFA moiety of the invention include, but are not limited to, Short-acting insulin (e.g., regular insulin), Rapid-acting insulins (e.g., insulin aspart, insulin glulisine, and insulin lispro), Intermediate-acting insulin (e.g., insulin isophane), Long-acting insulins (e.g., insulin degludec, insulin detemir, insulin glargine, and insulin glargine), Combination insulins (e.g., 70/30 (insulin aspart protamine-insulin aspart), 75/25 (insulin lispro protamine-insulin lispro), 50/50 (insulin lispro protamine-insulin lispro), 70/30 (human insulin NPH-human insulin regular), 70/30 (human insulin NPH-human insulin regular), and (insulin degludec-insulin aspart)), and Pramlintide, an amylinomimetic drug.

Chemotherapeutic Agents

In one embodiment, the method of the invention may comprise administration of the composition of the invention in combination with one or more chemotherapeutic agent. Chemotherapeutic agents include, but are not limited to, ara-C, daunomycin, cladribine (Leustatin, 2-CdA), cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium). In some embodiments, a composition of the invention is administered before, during, or after administration of at least one antiproliferative agent for the treatment of cancer. Antiproliferative agents are compounds that decrease the proliferation of cells. Antiproliferative agents include, but are not limited to, alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The compositions of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for combining with the compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the compositions of the invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride;

forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

Anti-Viral Agents

The present invention contemplates compositions comprising at least one SCFA or compound comprising a SCFA moiety as described herein in combination with anti-viral agents. Anti-viral agents include, but are not limited to, inhibitors of viral uncoating (e.g., amantadine and rimantidine), reverse transcriptase inhibitors (e.g., acyclovir, zidovudine, and lamivudine), agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddl, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir), abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

Antiparasitic Agents

The present invention contemplates compositions comprising at least one SCFA or compound comprising a SCFA moiety as described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Antibacterial Agents

The present invention contemplates compositions comprising at least one SCFA or compound comprising a SCFA moiety as described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

Methods of Treatment

One aspect of the invention relates to a treatment regimen for treating or preventing a disease or disorder using a composition of the invention. Administration of the compositions of the present invention to a subject may be carried out using known procedures, at dosages and for periods of time effective for treating or preventing a disease or disorder in the subject. An effective amount of the therapeutic compound necessary to achieve a therapeutic effect may vary according to factors such as the state of the disease or disorder in the subject; the age, sex, and weight of the subject.

The regimen of administration may affect what constitutes an effective amount. Further, the dosages of the compositions may be proportionally increased or decreased as indicated by the exigencies of the therapeutic or prophylactic situation. A non-limiting example of an effective dose range for a therapeutic compound of the invention is from about 1 to about 5,000 mg/kg of body weight/per day. The effective dose can be between 1 µg to 10 mg active component/kg body weight/time, and can be 20 µg to 10 mg component/kg body weight/time. The therapeutic compound can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of doses for effective treatment can be 1, 2, 3, 4, 5, 6, 7, 8, 9, 10 or more than 10.

One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the subject being treated, and like factors well known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

Compositions of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments there between.

In one embodiment, the treatment regimen comprises daily administration of a composition of the invention. In one embodiment, a treatment regimen comprises administering a short chain fatty acid at least once daily for at least 1 day, at least 2 days, at least 3 days, at least 4 days, at least 5 days, at least 7 days, at least 10 days, at least 2 weeks, at least 3 weeks, at least 1 month, at least 2 months, at least 3 months, at least 6 months, at least 1 year or more than 1 year. In one embodiment, a treatment regimen comprises administering a short chain fatty acid three times daily for at least 1 day, at least 2 days, at least 3 days, at least 4 days, at least 5 days, at least 7 days, at least 10 days, at least 2 weeks, at least 3 weeks, at least 1 month, at least 2 months, at least 3 months, at least 6 months, at least 1 year or more than 1 year. In one embodiment, a treatment regimen comprises administering a composition comprising a short chain fatty acid, a short chain fatty acid precursor, a short chain fatty acid biosynthesis precursor, or a combination thereof at least once daily upon appearance of a disease or disorder.

In one embodiment, a treatment regimen comprises daily oral administration of a short chain fatty acid. In one exemplary embodiment, 600 mg of butyrate is administered 3 times per day (a total of 1800 mg/day) for at least one week. In one embodiment, a treatment regimen comprises oral administration of two butyrate capsules containing 600 mg of butyrate 3 times per day (a total of 3600 mg/day) for at least one week. In one embodiment, a treatment regimen comprises oral administration of two butyrate capsules containing 600 mg of butyrate 3 times per day (a total of 3600 mg/day) for at least one week followed thereafter by oral administration of butyrate capsules containing 600 mg of butyrate 3 times per day (a total of 1800 mg/day) for at least one week.

As described herein, administration of a composition of the invention to an individual makes it possible to induce tolerance, strengthen gut barrier integrity, and reduce inflammation in the individual. The method comprises administering to an individual a composition described herein. In some embodiments, the composition comprises one or more SCFAs or SCFA derivatives. The composition is administered to the individual in sufficient quantity to produce the desired effect of inducing tolerance, strengthening the gut barrier, and reducing inflammation. It may be administered to an individual in need of treatment, reduction in the severity of or prevention of at least one disease selected from an autoimmune disease, an inflammatory disease, an allergic disease, or an infectious disease.

Whether administration of the composition induces tolerance can be determined by using, as an index, increase or reinforcement of at least one of the following: the number of regulatory T cells (Tregs), the ratio of Tregs in the T cell group of the colon, a function of Tregs, or expression of a marker of Tregs. A specific approach is measurement counts or percentage of Foxp3-expressing Tregs in a patient sample, such as a biopsy or a blood sample, promotion (enhancement) of IL-10 expression, promotion (enhancement) of CTLA4 expression, promotion (enhancement) of IDO expression, or suppression of IL-4 expression as the index of the induction of proliferation or accumulation of regulatory T cells. Whether administration of the composition strengthens barrier function can be determined by using, as an index, increase in production of active form TGF-$\beta$ and/or tight junction-related proteins by intestinal epithelial cells. Whether administration of the composition reduces inflammation can be determined by using, as an index, increase in production of anti-inflammatory cytokines such as IL-10 and/or TGF-.beta., or decrease in production of pro-inflammatory cytokines such as IL-4.

Methods for detecting such expression include northern blotting, RT-PCR, and dot blotting for detection of gene expression at the transcription level; ELISA, radioimmunoassays, immunoblotting, immunoprecipitation, and flow cytometry for detection of gene expression at the translation level. Samples that may be used for measuring such an index include tissues and fluids obtained from an individual, such as blood, a biopsy, or a fecal sample.

Pharmaceutical Compositions

The present invention includes pharmaceutical compositions comprising one or more compositions of the present invention. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Said compositions may comprise additional medicinal agents, pharmaceutical agents, carriers, buffers, adjuvants, dispersing agents, diluents, and the like depending on the intended use and application.

Examples of suitable pharmaceutical carriers, excipients and/or diluents are well known in the art and include, but are not limited to, a gum, a starch (e g. corn starch, pregelatinized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Pharmaceutically acceptable carriers for liquid formulations are aqueous or non-aqueous solutions, suspensions, emulsions or oils, Examples of non-aqueous solvents are propylene glycol, polyethylene glycol, and injectable organic esters such as ethyl oleate. Examples of oils are those of animal, vegetable, or synthetic origin, for example, peanut oil, soybean oil, olive oil, sunflower oil, turmeric oil, fish-liver oil, another marine oil, or a lipid from milk or eggs.

Aqueous carriers include water, alcoholic/aqueous solutions, emulsions or suspensions, including saline and buffered media such as phosphate buffered saline solutions, water, emulsions, such as oil/water emulsions, various types of wetting agents, sterile solutions etc. Compositions comprising such carriers can be formulated by well-known conventional methods. Suitable carriers may comprise any material which, when combined with the biologically active compound of the invention, retains the biological activity. Preparations for parenteral administration may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles may include sodium chloride solution, Ringer's dextrose, dextrose and sodium chloride, lactated Ringer's, or fixed oils. Intravenous vehicles may include fluid and nutrient replenishes, electrolyte replenishers (such as those based on Ringer's dextrose), and the like. Preservatives and other additives may also be present including, for example, antimicrobials, anti-oxidants, chelating agents, and inert gases and the like, in addition, the pharmaceutical composition of the present invention might comprise proteinaceous carriers, like, e.g., serum albumin or immunoglobulin.

The pharmaceutical compositions provided herein may also be administered as controlled-release compositions, i.e. compositions in which the active ingredient is released over a period of time after administration. Controlled- or sustained-release compositions include formulation in lipophilic depots (e.g. fatty acids, waxes, oils). In another embodiment, the composition is an immediate-release composition, i.e. a composition in which all the active ingredient is released immediately after administration.

Further, the pharmaceutical compositions according to the invention and as described herein in the various embodiments may or a composition comprising said compound may be administered admixed to food, functional food, drinks, medicinal food.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention are contemplated include, but are not limited to, humans and other primates, mammals including commercially relevant mammals such as non-human primates, cattle, pigs, horses, sheep, cats, and dogs, non-mammalian animals, and other veterinary applications.

Pharmaceutical compositions that are useful in the methods of the invention may be prepared, packaged, or sold in formulations suitable for ophthalmic, oral, rectal, vaginal, parenteral, topical, pulmonary, intranasal, buccal, intratumoral, epidural, intracerebral, intracerebroventricular, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

Pharmaceutical compositions also include nutritional compositions, such as oral nutritional compositions for oral consumption and optionally for enteral adsorption, wherein the nutritional composition includes the compounds of the present invention. Therefore, in one embodiment, the invention relates to nutraceutical compositions.

If the nutritional compositions are formulated to be administered orally, the compositions may be a liquid oral nutritional supplement (e.g., incomplete feeding) or a complete feeding. In this manner, the nutritional compositions may be administered in any known form including, for example, tablets, capsules, liquids, chewables, soft gels, sachets, powders, syrups, liquid suspensions, emulsions, infant formulas and solutions in convenient dosage forms.

A nutritional formula encompasses any nutritionally complete or supplementary formulation (a nutritional supplement, for example). As used herein, "nutritionally complete" are preferably nutritional products that contain sufficient types and levels of macronutrients (protein, fats and carbohydrates) and micronutrients to be sufficient to be a sole source of nutrition for the subject to which it is being administered to. Patients can receive 100% of their nutritional requirements from such complete nutritional compositions. According to one embodiment, the nutritional formula is a supplementary formulation providing supplementary nutrition. A "supplementary formula" may not be nutritionally complete, but preferably contains specific nutrients that are supportive, for example in combination with physical exercise, with further of the beneficial effects of the invention, and/or which address specific or additional needs of the subject.

The nutritional formula may be a generally applicable nutritional formula, for example adapted to subjects of a specific age, for example a formula for children, but it may also be a formula for elderly patients, for intensive care patients, or a specially adapted formula for patients suffering from a specific disease, for example. Any nutritional formula may be reconstitutable, that is, present in a substantially dried, for example powdered form, or ready-to-drink, in the form of liquid formulas, for example.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

The compositions of the present invention as described herein may be used as a complete food product, as a component of a food product, as a dietary supplement or as part of a dietary supplement, as a feed additive and may be either in liquid, semisolid or solid form. The compositions of the present invention as described herein additionally may be in the form of a pharmaceutical composition. The compositions, dietary supplements, food products, baby food products, feed additives, and/or pharmaceutical compositions of the present invention may advantageously be utilized in methods for promoting the health of an individual.

As indicated above, the compositions may be in liquid, semisolid or solid form. For example, the compositions may be administered as tablets, gel packs, capsules, gelatin capsules, flavored drinks, as a powder that can be reconstituted into such a drink, cooking oil, salad oil or dressing, sauce, syrup, mayonnaise, margarine or the like. Furthermore, the food product, dietary supplements, and the like, of the present invention can include, but are not limited to, dairy products, baby food, baby formula, beverages, bars, a powder, a food topping, a drink, a cereal, an ice cream, a candy, a snack mix, a baked food product and a fried food product. Beverages of the invention include but are not limited to energy drinks, nutraceutical drinks, smoothies, sports drinks, orange juice and other fruit drinks. A bar of the present invention includes, but is not limited to, a meal replacement, a nutritional bar, a snack bar and an energy bar, an extruded bar, and the like. Dairy products of the invention include, but are not limited to, including but not limited to yogurt, yogurt drinks, cheese and milk.

The food products or dietary supplements of the present invention may further comprise herbals, herbal extracts, fungal extracts, enzymes, fiber sources, minerals, and vitamins. The microalgal oils and microalgal biomass of the present invention may be used in the compositions of the invention for both therapeutic and non-therapeutic uses. Thus, the compositions, food products and animal feed additives of the present invention may be used for therapeutic or non-therapeutic purposes.

Compositions intended for oral administration may be prepared according to any known method for the manufacture of dietary supplements or pharmaceutical preparations, and such compositions may include at least one additive selected from the group consisting of taste improving substances, such as sweetening agents or flavoring agents, stabilizers, emulsifiers, coloring agents and preserving agents in order to provide a dietetically or pharmaceutically palatable preparation. Vitamins, minerals and trace element from any physiologically acceptable source may also be included in the composition of the invention.

A pharmaceutical composition of the present invention comprises the said compositions of the present invention in a therapeutically effective amount. The compositions may additionally comprise prescription medicines or non-prescription medicines. The combinations may advantageously produce one or more of the following effects: (1) additive and/or synergistic benefits; (2) reduction of the side effects and/or adverse effects associated with use of the prescription medicine in the absence of the said formulations; and/or (3) the ability to lower the dosage of the prescription medicine in comparison to the amount of prescription medicine needed in the absence of the said formulations.

The active agents of the present invention can be prepared in the form of their pharmaceutically acceptable salts. As understood by one of skill in the art, pharmaceutically acceptable salts are salts that retain the desired biological activity of the parent compound and do not impart undesired toxicological effects. "Pharmaceutically acceptable salts" as defined herein include derivatives of the disclosed SCFA or compound comprising a SCFA moiety, wherein the parent compound is modified by making non-toxic salts of the carboxylate group thereof, and further refers to pharmaceutically acceptable hydrates, and solvates of such compounds. Examples of pharmaceutically acceptable salts include, but are not limited to, mineral or organic acid salts of the carboxylic acid group of the SCFA. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxylmaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like. Lists of additional suitable salts may be found, e.g., in Remington's Pharmaceutical Sciences, 17th ed., Mack Publishing Company, Easton, Pa., p. 1418 (1985). In some embodiments the SCFA can be present as an ester of the SCFA's carboxylic acid with a branched or unbranched alkyl alcohol of one to 6 carbons. For example, the SCFA can be present as an ethyl ester, propyl ester, butyl ester, isopropyl ester, t-butyl ester, pentyl ester, or hexyl ester.

The active agents can be formulated for administration in accordance with known pharmacy techniques. See, e.g., Remington, The Science And Practice of Pharmacy (9th Ed. 1995). In the manufacture of a pharmaceutical composition according to the present invention, the active agents (including the physiologically acceptable salts thereof) is typically admixed with, inter alia, an acceptable carrier. The carrier must, of course, be acceptable in the sense of being compatible with any other ingredients in the formulation and must not be deleterious to the subject. The carrier can be a solid or a liquid, or both, and can be formulated with the active agent as a unit-dose formulation, for example, a tablet, which can contain from 0.01% or 0.5% to 95% or 99%, or any value between 0.01% and 99%, by weight of the active agent. One or more active agents can be incorporated in the compositions of the invention, which can be prepared by any of the well-known techniques of pharmacy, comprising admixing the components, optionally including one or more accessory ingredients. Moreover, the carrier can be preservative free, as described herein above.

In some embodiments, the active agents comprise a lower limit ranging from about 0.01, 0.02, 0.03, 0.04, 0.05, 0.06, 0.07, 0.08, 0.09, 1, 2, 3, 4, 5, 6, 7, 8, 9, and 10% to an upper limit ranging from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% by weight of the composition. In some embodiments, the active agent includes from about 0.05% to about greater than 99% by weight of the composition.

The pharmaceutical compositions according to embodiments of the present invention are generally formulated for oral or topical (i.e., skin, ocular and mucosal surfaces) administration, with the most suitable route in any given case depending on the nature and severity of the condition being treated and on the nature of the particular active agent which is being used.

Topical Formulations

The compositions of the present invention and the pharmaceutical compositions containing said compounds, may be administered topically, and thus be formulated in a form suitable for topical administration, i.e. as a pH balanced cream preparation. An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi liquid preparations such as liniments, lotions, oil in water or water in oil emulsions such as cremes, ointments or pastes, and solutions or suspensions. Further, formulations suitable for topical administration can be in the form of cremes and liquids including, for example, syrups, suspensions or emulsions, inhalants, sprays, mousses, oils, gels, solids and the like. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. In various embodiments, an active compound may be present in the amount of from about 0.0001% to about 15% by weight volume of the composition, from about 0.0005% to about 5% of the composition, or from about 0.001% to about 1% of the composition. Such compounds may be synthetically-or naturally derived.

Oral Formulations

The compositions of the present invention and the pharmaceutical compositions containing said compounds, may be administered orally, and thus be formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. If formulated in form of a capsule, the compositions of the present invention comprise, in addition to the active compound and the inert carrier or diluent, a hard gelating capsule. In one embodiment, a formulation for oral administration is an enteric coated, time release capsule.

Formulations suitable for oral administration can be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations can be prepared by any suitable method of pharmacy, which includes bringing into association the active compound and a suitable carrier (which can contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet can be prepared by compressing or molding a powder or granules containing the active compound, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

Formulations for Other Routes of Administration

The compositions of the present invention and the pharmaceutical compositions containing said compounds may be further administered intranasally, i.e. by inhalation and thus may be formulated in a form suitable for intranasal administration, i.e. as an aerosol or a liquid preparation.

The compositions of the present invention may also, for example, be formulated for parenteral administration. Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, desintegrators, fillers, and coating compositions. "Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et. al., (Media, Pa.: Williams and Wilkins, 1995) which provides information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert), or the like. For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, $6^{th}$ Ed. (Media, Pa.: Williams & Wilkins, 1995).

An exemplary method for preparing extended release tablets is by compressing a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are manufactured using compression rather than molding. A method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

Delayed release formulations are created by coating a solid dosage form with a film of a polymer which is insoluble in the acid environment of the stomach, and soluble in the neutral environment of small intestines. The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Exemplary coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, e.g., formed from acrylic acid, methacrylic acid, methyl acrylate, ethyl acrylate, methyl methacrylate and/or ethyl methacrylate, and other methacrylic resins that are commercially available under the tradename Eudragit®. (Rohm Pharma; Westerstadt, Germany), including Eudragit®. L30D-55 and L100-55 (soluble at pH 5.5 and above), Eudragit®. L-100 (soluble at pH 6.0 and above), Eudragit®. S (soluble at pH 7.0 and above, as a result of a higher degree of esterification), and Eudragits®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The particles can be prepared entirely from a therapeutic agent, or from a combination of the agent and a surfactant. The particles can be made of a variety of materials. Both inorganic and organic materials can be used. For example, ceramics may be used. Polymeric and non-polymeric materials, such as fatty acids, may be used to form aerodynamically light particles. Other suitable materials include, but are not limited to, gelatin, polyethylene glycol, trehalose, and dextran. Particles with degradation and release times ranging from seconds to months can be designed and fabricated, based on factors such as the particle material.

In addition to a therapeutic or diagnostic agent (or possibly other desired molecules for delivery), the particles can include excipients such as a sugar, such as lactose, a protein, such as albumin, and/or a surfactant.

Enteric Coated Capsules: "Gastric resistant natural polymer," as used herein, refers to natural polymers or mixtures of natural polymers which are insoluble in the acidic pH of the stomach. "Film-forming natural polymer," as used herein, refers to polymers useful for surface coatings that are applied by spraying, brushing, or various industrial processes, which undergo film formation. In most film-formation processes, a liquid coating of relatively low viscosity is applied to a solid substrate and is cured to a solid, high-molecular-weight, polymer-based adherent film possessing the properties desired by the user. For most common applications, this film has a thickness ranging from 0.5 to 500 micrometers (0.0005 to 0.5 millimeters, or 0.00002 to 0.02 inches).

"Gelling agent," as used herein, refers to substances that undergo a high degree of cross-linking or association when hydrated and dispersed in the dispersing medium, or when dissolved in the dispersing medium. This cross-linking or association of the dispersed phase alters the viscosity of the dispersing medium. The movement of the dispersing medium is restricted by the dispersed phase, and the viscosity is increased.

Gastric resistant film-forming compositions containing (1) a gastric resistant natural polymer; (2) a film-forming natural polymer; and optionally (3) a gelling agent, are described herein. Exemplary gastric resistant natural polymers include, but are not limited to, pectin and pectin-like polymers which typically consist mainly of galacturonic acid and galacturonic acid methyl ester units forming linear polysaccharide chains. Typically these polysaccharides are rich in galacturonic acid, rhamnose, arabinose and galactose, for example the polygalacturonans, rhamnogalacturonans and some arabinans, galactans and arabinogalactans. These are normally classified according to the degree of esterification. In high (methyl) ester ("HM") pectin, a relatively high portion of the carboxyl groups occur as methyl esters, and the remaining carboxylic acid groups are in the form of the free acid or as its ammonium, potassium, calcium or sodium salt. Useful properties may vary with the degree of esterification and with the degree of polymerization. Pectin, in which less than 50% of the carboxyl acid units occur as the methyl ester, is normally referred to as low (methyl) ester or LM-pectin. In general, low ester pectin is obtained from high ester pectin by treatment at mild acidic or alkaline conditions. Amidated pectin is obtained from high ester pectin when ammonia is used in the alkaline deesterification process. In this type of pectin some of the remaining carboxylic acid groups have been transformed into the acid amide. The useful properties of amidated pectin may vary with the proportion of ester and amide units and with the degree of polymerization. In one embodiment, the gastric resistant natural polymer is pectin. The gastric resistant natural polymer is present in an amount less than about 5% by weight of the composition, e.g., from about 2 to about 4% by weight of the composition.

Exemplary film-forming natural polymers include, but are not limited to, gelatin and gelatin-like polymers. In an exemplary embodiment, the film-forming natural polymer is gelatin. A number of other gelatin-like polymers are available commercially. The film-forming natural polymer is present in an amount from about 20 to about 40% by weight of the composition, e.g., from about 25 to about 40% by weight of the composition.

The compositions can optionally contain a gelling agent. Exemplary gelling agents include divalent cations such as $Ca^{2+}$ and $Mg^{2+}$. Sources of these ions include inorganic calcium and magnesium salts and calcium gelatin. The gelling agent is present in an amount less than about 2% by weight of the composition, e.g., less than about 1% by weight of the composition.

One or more plasticizers can be added to the composition to facilitate the film-forming process. Suitable plasticizers include glycerin, sorbitol, sorbitans, maltitol, glycerol, polyethylene glycol, polyalcohols with 3 to 6 carbon atoms, citric acid, citric acid esters, triethyl citrate and combinations thereof. The concentration of the one or more plasticizers is from about 8% to about 30% by weight of the composition. In one embodiment, the plasticizer is glycerin and/or sorbitol.

The film-forming composition can be used to prepare soft or hard shell gelatin capsules which can encapsulate a liquid or semi-solid fill material or a solid tablet (Softlet®) containing an active agent and one or more pharmaceutically acceptable excipients. Alternatively, the composition can be administered as a liquid with an active agent dissolved or dispersed in the composition.

The film-forming composition can be used to prepare soft or hard capsules using techniques well known in the art. For example, soft capsules are typically produced using a rotary die encapsulation process. Fill formulations are fed into the encapsulation machine by gravity.

The capsule shell can contain one or more plasticizers selected from the group consisting of glycerin, sorbitol, sorbitans, maltitol, glycerol, polyethylene glycol, polyalcohols with 3 to 6 carbon atoms, citric acid, citric acid esters, triethyl citrate and combinations thereof.

In addition to the plasticizer(s), the capsule shell can include other suitable shell additives such as opacifiers, colorants, humectants, preservatives, flavorings, and buffering salts and acids.

Opacifiers are used to opacify the capsule shell when the encapsulated active agents are light sensitive. Suitable opacifiers include titanium dioxide, zinc oxide, calcium carbonate and combinations thereof.

Colorants can be used to for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to inhibit cross-linking of the gelatin.

Soft or hard capsules can be used to deliver a wide variety of pharmaceutically active agents. Suitable agents include small molecules, proteins, nucleic acid, carbohydrates, lipids, and full organisms.

Fill formulations may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to surfactants, humectants, plasticizers, crystallization inhibitors, wetting agents, bulk filling agents, solubilizers, bioavailability enhancers, pH adjusting agents, and combinations thereof.

Alternatively, the composition can be administered as a liquid with an active agent dissolved (e.g. solution) or dispersed (e.g., suspension) in the composition. Suitable active agents are described above. The solution or suspension may be prepared using one or more pharmaceutically acceptable excipients. Suitable excipients include, but are not limited to, surfactants, humectants, plasticizers, crystallization inhibitors, wetting agents, bulk filling agents, solubilizers, bioavailability enhancers, pH adjusting agents, flavorants and combinations thereof.

Mucoadhesive Particles and methods of manufacturing: In general terms, adhesion of polymers to tissues may be achieved by (i) physical or mechanical bonds, (ii) primary or covalent chemical bonds, and/or (iii) secondary chemical bonds (e.g., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (e.g., Van der Waals interactions) and stronger specific interactions, which include hydrogen bonds. The hydrophilic functional groups responsible for forming hydrogen bonds are the hydroxyl (—OH) and the carboxylic groups (—COOH).

Adhesive polymeric microspheres have been selected on the basis of the physical and chemical bonds formed as a function of chemical composition and physical characteristics, such as surface area, as described in detail below. These microspheres are characterized by adhesive forces to mucosa of greater than 11 mN/cm$^2$. The size of these microspheres range from between a nanoparticle to a millimeter in diameter. The adhesive force is a function of polymer composition, biological substrate, particle morphology, particle geometry (e.g., diameter) and surface modification.

Classes of Polymers Useful in Forming Bioadhesive Microspheres: Suitable polymers that can be used to form bioadhesive microspheres include soluble and insoluble, biodegradable and nonbiodegradable polymers. These can be hydrogels or thermoplastics, homopolymers, copolymers or blends, natural or synthetic. A key feature, however, is that the polymer must produce a bioadhesive interaction between 110 N/m2 (11 mN/cm2) and 100,000 N/m2 when applied to the mucosal surface of rat intestine.

In order for bioadhesive particles to embed themselves or become engulfed in the mucus lining the GI tract, the radius of the individual particles should be as thick as the thickness of the natural mucous layer. It has been shown that the gastric mucous layer thickness typically varies from 5 to 200.mu. in the rat and 10 to 400.mu. in man. Occasionally, however, it can reach thicknesses as great as 1000.mu. in man, as described by Spiro, R. G., "Glycoproteins," Annual Review of Biochemistry, 39, 599-638, 1970; Labat-Robert, J. & Decaeus, C., "Glycoproteins du Mucus Gastrique: Structure, Fonction, et Pathologie," Pathologie et Biologie (Paris), 24, 241, 1979; Allen, A., Hutton, D. A., Pearson, J. P., & Sellers, L. A., "Mucus Glycoprotein Structure, Gel Formation and Gastrointestinal Mucus Function" in Mucus and Mucosa, Ciba Foundation Symposium 109 (eds. J. Nugent & M. O'Connor), pp. 137 (London: Pitman, 1984). In the past, two classes of polymers have appeared to show useful bioadhesive properties: hydrophilic polymers and hydrogels. In the large class of hydrophilic polymers, those containing carboxylic groups (e.g., poly[acrylic acid]) exhibit the best bioadhesive properties. One could infer that polymers with the highest concentrations of carboxylic groups should be the materials of choice for bioadhesion on soft tissues. In other studies, the most promising polymers were: sodium alginate, carboxymethylcellulose, hydroxymethylcellulose and methylcellulose. Some of these materials are water-soluble, while others are hydrogels.

Rapidly bioerodible polymers such as poly[lactide-co-glycolide], polyanhydrides, and polyorthoesters, whose carboxylic groups are exposed on the external surface as their smooth surface erodes, are excellent candidates for bioadhesive drug delivery systems. In addition, polymers containing labile bonds, such as polyanhydrides and polyesters, are well known for their hydrolytic reactivity. Their hydrolytic degradation rates can generally be altered by simple changes in the polymer backbone.

Representative natural polymers include proteins, such as zein, modified zein, casein, gelatin, gluten, serum albumin, or collagen, and polysaccharides, such as cellulose, dextrans, polyhyaluronic acid, polymers of acrylic and methacrylic esters and alginic acid. Representative synthetic polymers include polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof. Synthetically modified natural polymers include alkyl celluloses, hydroxyalkyl celluloses, cellulose ethers, cellulose esters, and nitrocelluloses. Other polymers of interest include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, poly(methyl methacrylate), poly(ethyl methacrylate), poly(butyl methacrylate), poly(isobutyl methacrylate), poly(hexyl methacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate)polyethylene, polypropylene, poly(ethylene glycol), poly(ethylene oxide), poly(ethylene terephthalate), poly(vinyl acetate), polyvinyl chloride, polystyrene, polyvinyl pyrrolidone, and polyvinylphenol. Representative bioerodible polymers include polylactides, polyglycolides and copolymers thereof, poly(ethylene terephthalate), poly(butic acid), poly(valeric acid), poly(lactide-co-caprolactone), poly [lactide-co-glycolide], polyanhydrides, polyorthoesters, blends and copolymers thereof.

The pharmaceutically acceptable compounds of the invention will normally be administered to a subject in a daily dosage regimen. For an adult subject this may be, for example, an oral dose of at least one SCFA or compound comprising a SCFA moiety of between 0.1 gram and 15 grams. In further embodiments, an oral dose of at least one SCFA or compound comprising a SCFA moiety can be between 0.5 gram and 10 grams. In still further embodiments, an oral dose of at least one SCFA or compound comprising a SCFA moiety can be between 0.5 grams and 6 grams.

The pharmaceutical compositions may be administered 1, 2, 3, 4 or more times per day. Thus in particular embodiments, compositions formulated, for example, for topical administration may be administered multiple times daily.

In one embodiment, compositions are contemplated comprising a 1:1 (w/w) ratio of a first and a second SCFA, wherein there may be 0.1, 0.2, 0.3, 0.4, 0.5, 0.6, 0.7, 0.8, 0.9, 1, 2, 3, 4, 5, 6, 7, 8, 9, or 10 grams of a first SCFA. In other embodiments there may be a 2:1, 3:1, 4:1, 5:1; 6:1, 7:1, 8:1, 9:1, or 10:1 (w/w) ratio of a first and a second SCFA, wherein there may be 0.1, 0.2, 0.3, 0.4, 0.5, 0.6, 0.7, 0.8, 0.9, 1, 2, 3, 4, 5, 6, 7, 8, 9, or 10 grams of a first SCFA. Of course, the ratio of a first and a second SCFA administered may be varied from that disclosed herein above. For example, any amount of a first SCFA including 0.1, 0.2, 0.3, 0.4, 0.5, 0.6, 0.7, 0.8, 0.9, 1, 2, 3, 4, 5, 6, 7, 8, 9, or 10 grams of a first SCFA may be administered with any amount of a second SCFA including 0.1, 0.2, 0.3, 0.4, 0.5, 0.6, 0.7, 0.8, 0.9, 1, 2, 3, 4, 5, 6, 7, 8, 9, or 10 grams of a second SCFA. Such amounts of either supplement may be admixed in one composition or may be in distinct compositions.

Kits

The invention also includes a kit comprising compounds useful within the methods of the invention and an instructional material that describes, for instance, the method of administering compositions of the invention as described elsewhere herein. In one embodiment, the kit comprises a composition of the invention.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: Treatment of Skin Disorders with Short Chain Fatty Acids

Psoriasis is a chronic auto-inflammatory disease that causes raised, red, scaly patches to appear on the skin. It typically affects the outside of the elbows, knees or scalp, though it can appear on any location. Some people report that psoriasis is itchy, burns and stings. Psoriasis is associated with other serious health conditions, such as diabetes, heart disease and depression.

Current treatments of psoriasis include topical (creams, ointments, and phototherapy) and systemic (oral and injected medications) therapies. Topical creams and ointments include corticosteroids (overuse can cause skin thinning and resistance), retinoids, anthralin (normalizes skin cell growth) and vitamin D analogs (treatment with retinoids, anthralin or vitamin D analogs can irritate skin), calcineurin inhibitors (disrupt T-cell activation, continuous use is associated with increased risk of skin cancer and lymphoma), as well as nonprescription moisturizers and salicylic acid.

Phototherapy (UV light) includes the use of ultraviolet A (UVA) or ultraviolet B (UVB) lights either alone or in combination with medications. Short-term side effects include nausea, headache, burning and itching. Long-term side effects include dry and wrinkled skin, freckles, and increased risk of skin cancer, including melanoma.

Currently available systemic psoriasis therapies involve the use of retinoids (side effects may include lip inflammation, hair loss, and severe birth defects: women must avoid pregnancy for at least three years after taking the medication); chemotherapeutic drugs such as methotrexate and cyclosporine (may cause a number of serious side effects, including liver damage, decreased production of red and white blood cells and platelets, increased risk of infections and cancer); and immunomodulatory drugs or biologics (have strong effects on the immune system and may permit life-threatening infections). The side effects and high toxicity of the currently available treatments are undesirable for many patients suffering psoriasis.

SCFAs have never been used to treat any form of psoriasis. A major advantage of this approach is that there is little to no toxicity relative to other currently available treatments. SCFAs were given orally up to three times a day for as long as 3 weeks. The dose schedule was one to two (1-2) 600 mg butyrate pills 3 times daily for 7 days to 4 weeks followed by one (1) 600 mg butyrate pill 3 times daily for several weeks to several months. Sodium, magnesium or calcium salts of butyrate were used for these treatments. When treatment was discontinued, psoriasis skin lesions reappeared. When treatments were started again, lesions disappeared once more. The immediate pre- and post-treatment results from 4 individuals taking butyrate are shown in FIG. 2 through FIG. 5. Individuals with psoriasis taking butyrate capsules orally for 3-4 weeks showed marked improvement or complete resolution of skin lesions.

For example, clinical trials can evaluate different combinations and dose schedules of selected SCFAs in healthy individuals (Phase 1) and among patients with psoriasis (Phase II).

For example, the toxicity of single or combinations of SCFA is evaluated in a dose escalation study to determine the level of toxicity and what tissues or organs are affected. Pharmacokinetic (PK) studies are to be conducted in mice to optimize the oral dose for further preclinical work. In the latter category, it will be important to see whether the molecules that are thought to mediate the pathogenesis of psoriasis in prior mouse studies are the same pathways inhibited in mice treated with SCFAs. For this work, two mouse models of psoriasis will be used. These preclinical studies will also be validated by prior human studies showing that the pro-inflammatory molecules targeted by SCFAs in mice with psoriasis are the same ones that appear to mediate psoriasis in people. This work will determine whether oral administration of SCFAs resolves psoriasis lesions in mice. This appears to be the case in humans taking butyrate orally. To optimize the dosage of a cream containing SCFAs, the cream will be applied to some but not other lesions in mice with psoriasis. If only the treated lesions resolve, then the effect of SCFAs is local, but if application to some lesions results in resolution of all lesions, then the effect of SCFAs is probably mediated by their systemic distribution. Depending upon the results, parallel clinical trials will be performed in patients.

The materials and methods used in the experiments are now described.

Materials and Methods

SCFAs

SCFAs, consisting of sodium butyrate, magnesium butyrate, and calcium butyrate were purchased commercially and manufactured by BodyBio.

Treatment with SCFAs

In all cases, no additional medication for psoriasis treatment was used during the butyrate regimen.

600 mg butyrate was administered orally 3 times daily to subjects having moderate to severe psoriasis for at least 2 weeks. 1200 mg butyrate was administered orally 3 times daily to a subject having severe psoriasis for 3 weeks followed by administration of 600 mg butyrate orally 3 times daily for an extended period of time.

Lesions were evaluated before and after treatment.

The results of the experiments are now described.

FIG. 1 depicts a diagram showing signaling pathways that are affected by SCFAs. Of the proteins included on the diagram, IL-18, TLR3, IFN-γ, TNFα, TGF-β, MyD88, PI3K/Akt, JAK/STAT, Smad 2/3, Smad 4 and IL-10 were found to be downregulated by SCFA treatment. The levels of IL-6, TRIF, PKR, TRAF2, TAK1 and TRAF6 were not evaluated for this study.

Figures 2A, 2B, 2C:
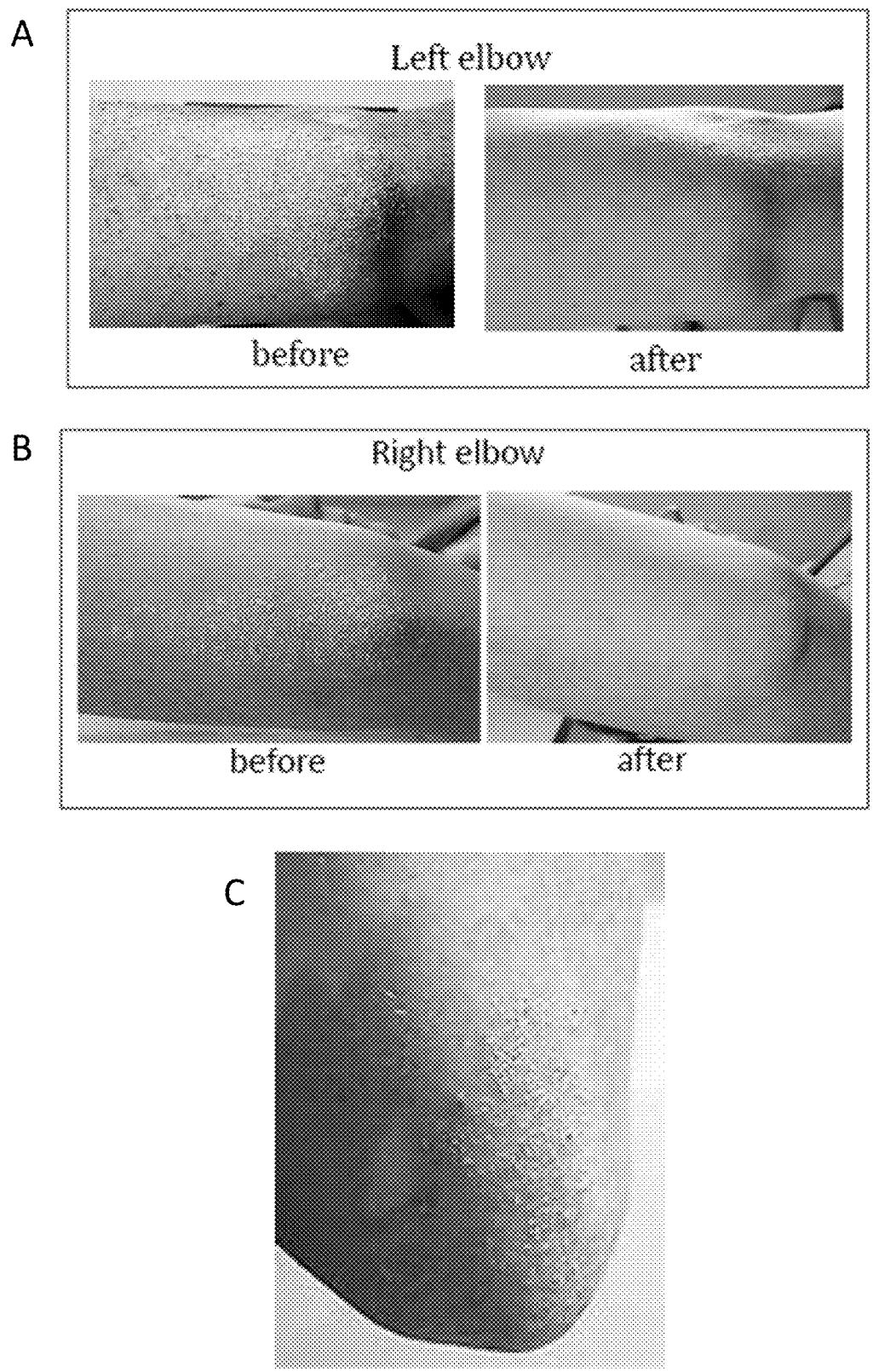
FIG. 2A through FIG. 2C, depicts images from a psoriasis patient undergoing a butyrate treatment regimen. The treatment regimen used was one (1) 600 mg butyrate pill 3 times daily for 16 days.

FIG. 2 shows results from a psoriasis patient undergoing a butyrate treatment regimen. The treatment regimen used was one (1) 600 mg butyrate pill 3 times daily for 16 days. Images are of the patient's left elbow before and after treatment, the patient's right elbow before and after treatment, and the re-emergence of psoriasis on the patient's left elbow after 20 days the patient ceased the butyrate treatment regimen.

Figure 3:
FIG. 3 depicts images from another psoriasis patient undergoing a butyrate treatment regimen. The treatment regimen used was two (2) 600 mg butyrate pill 3 times daily for 10 days, then regimen was one (1) butyrate pill, three times/day for three weeks.
Figure 3:

FIG. 3 shows results from another psoriasis patient undergoing a butyrate treatment regimen. The treatment regimen used was two (2) 600 mg butyrate pill 3 times daily for 10 days, then regimen was one (1) butyrate pill, three times/day for three weeks.

Figure 4:
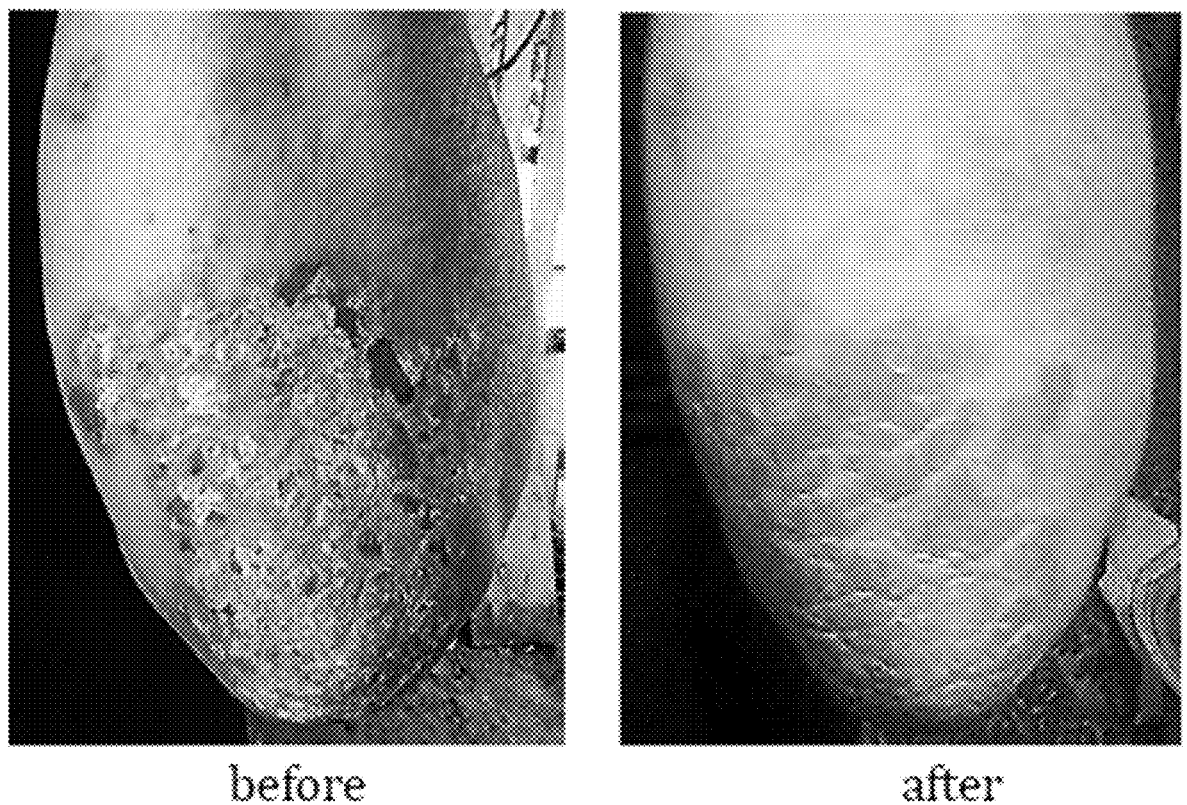
FIG. 4 depicts images from a third psoriasis patient undergoing a butyrate treatment regimen. The treatment regimen used was two (2) 600 mg butyrate pills 3 times daily for 7 days then one (1) 600 mg butyrate pill 3 times daily for 24 days. Images are of the patient's left elbow before and after treatment. The patient consumed elevated doses of alcohol during the treatment period.

FIG. 4 shows results from a third psoriasis patient undergoing a butyrate treatment regimen. The treatment regimen used was two (2) 600 mg butyrate pills 3 times daily for 7 days then one (1) 600 mg butyrate pill 3 times daily for 24 days. Images are of the patient's left elbow before and after treatment. The patient consumed elevated doses of alcohol during the treatment period.

Figures 5A, 5B, 5C:
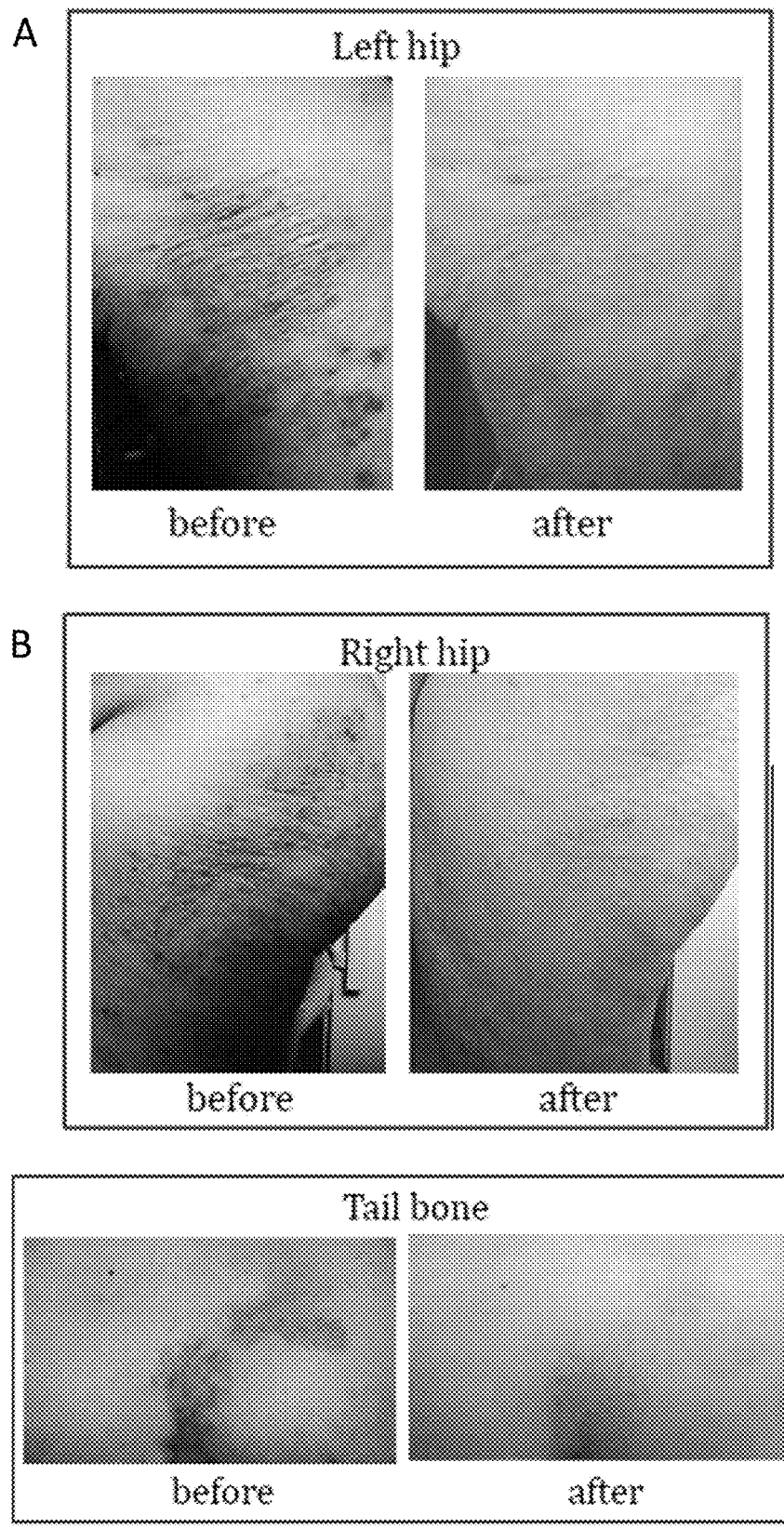
FIG. 5A through FIG. 5C, depicts images from a fourth patient with severe psoriasis over about 50% of the skin undergoing a butyrate treatment regimen. Patient started regimen as two (2) 600 mg butyrate pills 3 times daily for 4 weeks followed by one (1) 600 mg butyrate pill 3 times daily for several months. There was significant improvement, and no side effects were noted during the treatment for long period of time. To confirm that observed positive effects were due to treatment with our formulation, patient was asked to stop regimen. Psoriasis came back in about 20-25 days (pictures before). Patient started regimen as two (2) 600 mg butyrate pills 3 times daily for 10 days then one (1) 600 mg butyrate pills 3 times daily for 3 weeks and psoriasis disappeared (pictures after).

FIG. 5 shows results from a fourth patient with severe psoriasis over about 50% of the skin undergoing a butyrate treatment regimen. Patient started regimen as two (2) 600 mg butyrate pills 3 times daily for 4 weeks followed by one (1) 600 mg butyrate pill 3 times daily for several months. There was significant improvement, and no side effects were noted during the treatment for long period of time. To confirm that observed positive effects were due to treatment with our formulation, patient was asked to stop regimen. Psoriasis came back in about 20-25 days (pictures before). Patient started regimen as two (2) 600 mg butyrate pills 3 times daily for 10 days then one (1) 600 mg butyrate pills 3 times daily for 3 weeks and psoriasis disappeared (pictures after). Images are of the patient's left hip before and after treatment the second treatment regimen, the patient's right hip before and after the second treatment regimen, and the patient's tailbone before and after the second treatment regimen.

Figure 6:
FIG. 6 depicts images from a patient with a plaque psoriasis. An initial treatment regimen used was two (2) 600 mg butyrate pills 3 times daily for 20 days, then regimen was with a reduced dose, one (1) 600 mg butyrate pills 3 times daily for 25 days. Significant improvement was observed 3-5 months after he stopped his treatment. Patient was not taking any medicine before (at least 3 months), during and after treatment (at least 2 months).
Figure 6:
Figure 6:

FIG. 6 shows results from a patient with plaque psoriasis. An initial treatment regimen used was two (2) 600 mg butyrate pills 3 times daily for 20 days, then regimen was with a reduced dose, one (1) 600 mg butyrate pills 3 times daily for 25 days. Significant improvement was observed 3-5 months after he stopped his treatment. Patient was not taking any medicine before (at least 3 months), during and after treatment (at least 2 months).

Suggested Treatment:

|  | Amount/capsule | Daily dose |
| --- | --- | --- |
| Butyric acid | 900 (or 1800) mg | 3600 mg |
| Propionic acid | 100 (or 200) mg | 400 mg |
| Magnesium | 10 (or 20) mg | 40 mg |
| Vitamin D3 | 50 (or 100) IU | 200 IU |

Example 2: Combination Treatment of Skin Disorders Using Short Chain Fatty Acids This example is based, in part, on the discovery that administration of at least one SCFA in combination with at least one second compound is an effective approach for treating skin disease and disorders, including psoriasis. Without being bound by theory, it is expected that the combination of at least one SCFA with at least one second compound will provide an effective treatment for skin disorders. Additional compounds that are contemplated for use include a PDE4 inhibitor, an anti-inflammatory compound, a disease-modifying antirheumatic drug (DMARD), an immunosuppressant, a biologic agent, a Cox-2 inhibitor, apremilast or a combination thereof, and/or another agent. Non-limiting examples of these and other compounds useful in the invention are provided supra.

Suggested Treatment:

Combination treatment with apremilast: the daily oral dose is 1-2 g of butyrate, 100 mg propionate, 10-15 mg apremilast, 10-20 mg Magnesium, 80-100 IU Vitamin D3, 50-100 IU Vitamin E (d-alpha-tocopherol acetate).

Palm and feet psoriasis is poorly responsive to treatment (these parts of the body are constantly "disturbed" from everyday activities). The impact of hand and foot psoriasis on patients' quality of life is extremely high (patients are unable to wear shoes comfortably or use their hands).

For such psoriasis, combination with topical ointments is important. The daily oral dose of SCFAs formulation should be used accompanied with applying ointment consisting of:

⅖ part clobetazol (0.05%),
⅕ part calcipotriene (vit D, 0.005%),
⅕ part salicylic acid (10%),
⅕ part vit E (0.5%).

All these components (separately) are used as topical treatment.

Example 3: Use of Short Chain Fatty Acids in the Treatment of Eye Diseases and Disorders Uveitis onset is often sudden, and the treatment and prognosis of various uveitis entities vary greatly. Delayed treatment can lead to serious complications (detachment, blindness). It is critical first to use powerful drugs to stop disease progression. SCFAs can be used (orally and/or in the form of eyedrops) to sustain achieved therapeutic effect (in particular, reduce inflammation). This will eliminate negative side effects (including glaucoma, cataract) which are usually observed after prolonged treatment with biologics and steroids (as in case of chronic or autoimmune uveitis). SCFAs can be also used in the mixture with antibiotics (as eyedrops) and/or steroids (given at reduced doses).

Clinical trials evaluate different combinations and dose schedules of SCFA in healthy individuals (Phase 1) and among patients with uveitis (Phase II). Because some cases of uveitis are associated with a bacterial or viral infection, the formulation also may contain appropriate antibiotics or anti-viral compounds, respectively, along with the SCFAs.

Additional research includes testing single or combinations of SCFA in a dose escalation study to evaluate toxicity, and what form that toxicity takes (i.e., what tissues or organs are affected). Pharmacokinetic (PK) studies may be conducted in mice to understand what oral doses should be used for further preclinical work. It will be important to see whether the molecules that are thought to mediate the pathogenesis of uveitis in prior animal studies are the same pathways inhibited in animal models treated here with SCFAs.

For this work, two mouse models of uveitis are used. In one model, experimental autoimmune uveitis (EAU) is triggered by immunization with the retinal antigens S-ag and IRBP coupled to Complete Freund's Adjuvant (CFA) and a

*B. pertussis* toxin boost. The second model uses a IRBP161-180 peptide specific transgenic T cell receptor on a B10.RIII background, which then develops spontaneous uveitis. These preclinical studies are also be validated by prior human studies showing that the pro-inflammatory molecules targeted by SCFAs in mice with uveitis are the same molecules that appear to mediate uveitis in humans. This work confirms that oral administration of SCFAs resolves uveitis lesions in mice.

Dry eye occurs when the quantity and/or quality of tears fail to keep the surface of the eye sufficiently lubricated. Tears consist of oils, water, mucus, and more than 1500 different proteins that protect eyes. Vision in a dry eye disease may be affected because tears play an important role in light focusing. Factors that can contribute to dry eye include medications (antihistamines, antidepressants, birth control pills, medications for Parkinson's disease, high blood pressure etc.), aging, rosacea, autoimmune disorders (Sjögren's syndrome, lupus, scleroderma, etc.), vitamin A deficiency, etc.

As a result, tears in an outer (lipid layer) produced by the Meibomian glands, a middle (aqueous layer) produced by the lacrimal glands, and an inner (mucin layer) produced by goblet cells became compromised.

The frequent use of artificial tears or other lubricating eye drops is the main dry eye treatment. However, if dry eye is associated with inflammation, cyclosporine A, corticosteroids, tacrolimus, tetracycline derivatives, etc. are used (such treatment demonstrated measurable clinical improvement). In such cases, butyrate treatment could be useful.

Behçet's Disease (BD) is an autoimmune reaction that causes blood vessels (including eye blood vessels) to become inflamed (BD of the Eye). Inflammation inside of the eye occurs in more than half of those with BD and can cause blurred vision, pain, and redness. Other symptoms of the disease include blood clots and inflammation in the central nervous system and digestive organs. Some people may become blind or severely disabled. Corticosteroids and medications that suppress the immune system may be prescribed to reduce inflammation.

Although the disease occurrence is mainly associated with a genetic factor (human leukocyte antigen (HLA)-B51 antigen), molecular mechanisms involve increased neutrophil motility, elevated production of TNF-α and IL-17 and decreased production of IL-10 (all of which are regulated by SCFAs). It was shown that anti-TNF-α therapy suppresses effector T-cell differentiation in BD patients with uveitis. Since butyrate suppresses TNF-α, treatment with SCFAs (orally) may provide protection from inflammation in BD.

Inflammation after cataract surgery can be persistent. Although corticosteroids and non-steroidal anti-inflammatory drugs (NSAIDs) are used to treat inflammation (prophylactically or post-operatively), there are no established guidelines for the treatment of inflammation induced by cataract surgery. The long-term use of corticosteroids has raised safety concerns, especially with regard to elevated intraocular pressure. Surgical trauma triggers the arachidonic acid cascade (which are converted to prostaglandins (PG) by activated COX-1 and COX-2 enzymes), and PG are the most important inflammation mediators in this disease. Since butyrate was shown to inhibit COX-2 expression and PG production it can be used for treatment (in eyedrops).

Based on animal data, SCFA oral doses should be high to have a therapeutic effect.

Suggested Treatment:

The daily oral dose is 4-5 g of butyrate and 1.5-2 g of propionate in enteric coated, extended release capsules, twice/day.

Eyedrops containing 20-30 μM of both butyrate and 10-20 μM propionate (since blood plasma concentrations of these SCFAs are up to ~30 μM) can be also used.

In case of dry eyes, eyedrops should be given continuously, twice/day in combination with lubricants.

In other eye diseases, eyedrops should be given four times/day (in case of disease flares), and twice/day up to few months, in combination with oral doses of SCFAs.

SCFAs can be used in the mixture with antibiotics and/or steroids.

For example, in case of infectious uveitis: during first 3-5 days, use eyedrops (or eye injection) with antibiotics/steroids (at the doses prescribed by doctors), then during following 2-3 weeks, use eyedrops containing a mixture of SCFAs (20-30 μM) and antibiotics/steroids (at half of the prescribed doses), then continue eyedrops with SCFAs (20-30 μM) only. Based on the type of disease and severity, oral SCFAs could be given as well, alone or in combination with antibiotics. This could accelerate healing and minimize side effects.

Treatment of an Individual with Uveitis Using SCFA

Experiments were designed to treat a subject having infectious uveitis. In some instances, butyrate is administered to the subject. After completion of the butyrate therapy, the subject experiences significantly reduced inflammation.

Example 4: Use of Short Chain Fatty Acids in the Treatment of Macular Degeneration Age related macular degeneration (AMD) causes damage to the macula (a small area in the center of the retina). In the dry form of AMD, lipid aggregates (drusen) accumulate in the retina. The late stage of dry AMD (geographic atrophy) is characterized by degeneration of retinal pigment epithelium cells and the overlying light-sensing retinal photoreceptors. "There is no way to treat dry AMD." The Age-Related Eye Disease Studies (AREDS) found that daily intake of high-dose vitamins (vitamins E and C) and minerals (zinc oxide) can slow progression of the disease. In wet AMD, choroidal neovascularization occurs (newly immature blood vessels grow toward the outer retina from the underlying choroid). These blood vessels leak fluids and cause scarring of the macula. The major factor that contributes to vascularization is vascular endothelial growth factor (VEGF). Most widely used anti-angiogenic FDA-approved therapies (eye injection) include pegaptanib, lucentis and VEGF-TRAP-Eye (Ambati J, Fowler B J. Mechanisms of age-related macular degeneration. Neuron, 2012; 75(1):26-39), which improve or stabilize vision in the majority of patients. Butyrate was found to repress angiogenesis in vitro and in vivo and reduce expression of pro-angiogenesis factors, including hypoxia inducible factors (HIF-1a) and VEGF (Canani B, Di Costanzo M, Leone L. The epigenetic effects of butyrate: potential therapeutic implications for clinical practice. Clinical Epigenetics, 2012; 4(1):4). Therefore, butyrate can be used for AMD treatment (eyedrops).

Clinical trials can evaluate different combinations and dose schedules of selected SCFAs in healthy individuals (Phase 1) and then among patients with adult macular degeneration (AMD) (Phase II). Some studies have shown a modest improvement in advanced AMD by eating a Mediterranean diet, so some human trials may combine this diet with SCFA to look for additive or synergistic effects. However, human trials could take up to 2 or more years to see statistically significant results.

Additional research can include testing single or combinations of SCFAs (+/− dietary anti-oxidants) in a dose escalation study to look for toxicity, and what form that toxicity takes (i.e., what tissues or organs are affected). Pharmacokinetic (PK) studies can also be conducted in mice to get an idea of what oral doses should be used for further preclinical work. In the latter category, it can be important to see whether the molecules that are thought to mediate the pathogenesis of macular degeneration in prior animal studies are the same pathways inhibited in animal models treated here with SCFAs.

For this work, two mouse models of AMD can be used. In one model of dry AMD, a novel murine model of immune mediated retinal degeneration was induced by immunization with carboxyethylpyrrole (CEP)-modified albumin (CEP-MSA). CEP albumin adducts generated in the retinal photoreceptors in response to oxidative stress. Patients with AMD also have circulating CEP autoantibodies. In another model, CCL2/CX3CR1 KO mice, which are deficient in macrophage/retinal microglia migration (and recruitment), develop degenerative changes characteristic of some AMD lesions within 4-6 weeks of age. Here, the tissue response to oxidative stress is not functional (repair vs. continuing inflammation). Given that SCFAs block oxidative stress, block angiogenesis (by down-regulating expression of VEGF and PDGF), and down-regulate inflammatory responses, they may be effective in preventing and/or resolving AMD. Such preclinical studies can be validated by prior human studies showing that the pro-inflammatory molecules targeted by SCFAs in mice with AMD are the same ones that are associated with AMD in people. This work can confirm that oral administration of SCFAs resolves AMD lesions in mice.

Suggested Treatment:

The daily oral dose is 4-5 g of butyrate and 1.5-2 g of propionate in enteric coated, extended release capsules, twice/day.

Eyedrops containing 20-30 µM of both butyrate and 10-20 µM propionate (since blood plasma concentrations of these SCFAs are up to ~30 µM) can be also used. Eyedrops should be given four times/day (in case of disease flares), and twice/day up to few months, in combination with oral doses of SCFAs.

SCFAs can be used in the mixture with antibiotics and/or steroids.

Example 5: Treatment and Prevention of Autoimmune and Allergic Diseases in C-Section Delivered Neonates with Short Chain Fatty Acids Infants born by Cesarean section (C-section) experience an increased risk of type 1 diabetes (Cardwell et al., 2008, Diabetologia, 51(5):726-35) and asthma (Thavagnanam et al., 2008, Clin Exp Allergy, 38(4):629-33). These infants (born either at term or prematurely) acquire a gut microbiome which is characteristic of the maternal skin, and not the birth canal. This leaves the newborns susceptible to the development of allergic and autoimmune diseases and disorders, including allergic rhinitis, gastroenteritis, inflammatory bowel disease, asthma, juvenile rheumatoid arthritis, food allergies, obesity, and type 1 diabetes. The number of C-sections rose in the U.S. by about 50% between 1996-2005, when it reached 30.2%, which is much higher than the optimal limit of 10-15% as recommended by WHO. Other countries with rates greater than 20% include Canada, the United Kingdom, Mexico, and Brazil, suggesting that increasing numbers of infants will be at risk for allergic and autoimmune diseases. The rate of C-sections for second births, after a first child has been delivered by C-section, is about 90%. Presently, there are no standard treatments for these and other allergic/autoimmune diseases that may appear after C-section delivery. Some clinics try to partially restore the mother's missing microbes to babies born via C-section by swabbing those infants with their mother's vaginal fluid within two minutes of birth. However, this practice is controversial. There is even evidence that this approach can inadvertently expose infants to maternal diseases.

Experiments were designed to assess the efficacy of using SCFAs to prevent, delay, or augment the onset of at least one autoimmune and/or allergic disease or disorder in a subject. As discussed herein, infants delivered by C-section experience an elevated risk of developing autoimmune and allergic diseases and disorders, and the number and frequency of C-sections is increasing. Therefore, experiments were designed to deliver SCFAs to an expectant mother or a neonate delivered by C-section to prevent at least one autoimmune and/or allergic disease or disorder disclosed herein.

The one or more SCFAs of the invention can be given orally up to three times a day for as long as two months. The dose schedule can be ingestion of 6 tablets per day (600 mg/tablet) for one week, followed by 3 tablets per day (600 mg/tablet) until the C-section is performed. Sodium, magnesium, or calcium salts of SCFAs can be used for these treatments. Alternatively, if a pregnant woman expecting a C-section is not given SCFAs, the SCFAs could be mixed into food or drink provided to the infant.

In some aspects, experiments were designed to have the SCFAs be developed as supplements or nutraceuticals. Alternatively, the SCFAs can be repackaged as enteric coated capsules that deliver time released product(s) for maternal use, or added as a supplement to baby formula or food for at least the first 6-12 or 18-24 months of life. Clinical trials can evaluate different combinations and dose schedules of selected SCFAs in healthy individuals (Phase I) and then among women giving birth via C-section and to infants born to women via C-section (Phase II).

Additional experiments were designed to include testing single or combinations of SCFAs in a dose escalation study to look for toxicity, and what form that toxicity takes (i.e., what tissues or organs are affected). Pharmacokinetic (PK) studies can also be conducted in mice to get an idea of what oral doses should be used for further preclinical work. In the latter category, it is important to see whether the molecules that are thought to mediate the pathogenesis of the appropriate allergic or autoimmune diseases in prior mouse studies are the same pathways inhibited in mice treated with SCFAs. For this work, appropriate mouse models can be used. These preclinical studies can also be validated by prior human studies showing that the pro-inflammatory molecules targeted by SCFAs in the mouse models are the same ones that appear to mediate the corresponding diseases in people. This work can determine whether oral administration of SCFAs resolves the relevant diseases or disorders (e.g., lesions) in mice. Parallel clinical trials can be performed in women expecting C-section delivery during late pregnancy and among newborns that have arrived by C-section.

A major advantage of this approach is little to no toxicity relative to other currently available treatments, and at the same time, helping to re-establish gut homeostasis.

Infants born by C-section usually do not receive any interventions on a regular basis. However, Similac Pro-Advance and Similac Pro-Sensitive have human milk oligosaccharides, which are prebiotic, like that found in most breast milk. The present example contemplates a combination of one or more SCFAs with one or more of these products.

Suggested Treatment:

For breastfed infants: the daily oral dose for healthy mothers is 1-2 g of butyrate and 0.5-1 g of propionate and acetate in enteric coated, extended release capsules, 3 times/day during first month, then half of that dose during next 3 months.

In the article (Xu J, Chen X, Yu S, et al. Effects of Early Intervention with Sodium Butyrate (SB) on Gut Microbiota and the Expression of Inflammatory Cytokines in Neonatal Piglets. PLoS One, 2016; 11(9):e0162461), early intervention with sodium butyrate modulated the ileum inflammatory cytokines in neonatal piglets with low impact on intestinal microbial structure, which suggests oral administration of SB may have a benefit role in the health of neonatal piglets (1 and 7 days old). The oral dose was ~10 ml of 150 mmol/L (piglets consumed 10 ml of ~150 mmol/L of sodium butyrate which is equivalent to ~165 mg). For supplementation in formula, a suggested treatment regimen is using escalation doses: start with low concentrations (daily dose is 80-100 mg of butyrate, 20-30 mg of acetate and propionate during first month), then increase dose to 100-120 mg of butyrate and 30-40 mg of acetate and propionate during next 3-5 months).

Example 6: Use of Short Chain Fatty Acids in the Treatment of Vasculitis

Vasculitis is a rare autoimmune disease which involves inflammation of the blood vessels, arteries, veins or capillaries and can affect people of all ages. Vasculitis also may be linked to certain blood cancers (leukemia and lymphoma). Different types of vasculitis are classified according to the size and location of the blood vessels that are affected. Common vasculitis treatment includes corticosteroids and cytotoxic drugs. Some molecular mechanisms of the pathogenesis of vasculitis are outlined in our patent application. GPR-109a pathway was also shown to play an important role (Chai J T, Digby J E, Choudhury R P. GPR109A and vascular inflammation. Curr. Atheroscler. Rep. 2013; 15(5): 325). Activation of GPR-109a receptor down-regulates NF-κB, and a number of selective GPR109A agonists have been developed by Merck, GSK and other companies. This receptor is activated by butyrate (at EC50~1.5 mM) and niacin.

Clinical trials will evaluate different combinations and dose schedules of selected SCFAs in healthy individuals (Phase I) and then among patients with vasculitis (Phase II). At this point, cyclophosphamide or glucocorticoids are used most often for treatment, although methotrexate, azathioprine and mycophenolate have also been used. The problem is that these are highly toxic therapeutic approaches that limit their application in patients. More specific biologic therapies using monoclonal antibodies against TNFβ, IL-1 or IL-6 require evaluation. Given that the inflammatory processes in atherogenesis, most forms of vasculitis, and aneurysms share many characteristics, it is likely that intervention with SCFAs will show broader application in re-establishing homeostasis among these various disease states.

Additional research will include testing single or combinations of SCFAs in a dose escalation study to look for toxicity, and what form that toxicity takes (i.e., what tissues or organs are affected). Pharmacokinetic (PK) studies will also have to be conducted in mice to get an idea of what oral doses should be used for further preclinical work. In the latter category, it will be important to see whether the targets that are thought to mediate the pathogenesis of vasculitis in animal studies are the same targets/pathways inhibited in animal models treated here with SCFAs.

For this work, two mouse models of ANCA associated vasculitis can be used, since these are fairly well characterized. In one model, MPO knockout mice (MPO−/− mice) are immunized with MPO. These animals are then irradiated and reconstituted with syngeneic, wild type bone marrow. Since antibody producing plasma cells are relatively radio-resistant, circulating anti-MPO levels are maintained. The bone marrow reconstitutes neutrophils which are then available to bind anti-MPO. Mice then develop crescentic glomerulonephritis and urine abnormalities by 8 weeks post bone marrow transplant. Without being bound by any particular theory, given that neutrophils expressing MPO is also a target in human vasculitis, and that SCFAs down-regulate MPO expression by blocking NF-κB activity in macrophages (thereby blocking the secretion of factors by macrophages that activate neutrophils), it is proposed that the administration of SCFAs can block the development of vasculitis in this animal model.

Another model involves immunization of wild type C57BL/6 mice with human or mouse MPO, leading to the induction of both humoral and cellular responses to MPO. While this alone does not result in disease, the passive transfer of polyclonal glomerular binding antibody results in the accumulation of neutrophils into the glomeruli. The MPO in these neutrophils is then targeted by antigen specific CD4+ T cells, resulting in autoimmune glomerulonephritis, which is seen in about 50% of patients with ANCA vasculitis. Other animal models are available if needed. Without being bound by any particular theory, given that SCFAs promote the differentiation of T cells to the Treg phenotype, it is hypothesized that the administration of SCFAs can block or ameliorate the development of autoimmune glomerulonephritis.

Such preclinical studies can be validated by prior human studies in the literature showing that the pro-inflammatory molecules targeted by SCFAs in mice with vasculitis are the same ones that are associated with vasculitis in people. This work can determine whether oral administration of SCFAs resolves vasculitis in mice.

The models outlined in this Example may not cover all aspects of vasculitis pathogenesis, and for many forms of vasculitis, there is no animal model available. For example, regarding ANCA vasculitis, there is no reproducible model of granulomatous PR3-ANCA. However, the models used can establish proof-of-principle as to whether SCFAs should be taken into human clinical trials against vasculitis.

Suggested Treatment:

The daily oral dose is 5-6 g of butyrate in enteric coated, extended release capsules, 3 times/day, during first month, then 3-4 g of butyrate, twice a day, during several months. High doses should be used in case of flares.

Butyrate could be used in combination with reduced doses of steroids and chemodrugs.

Example 7: Use of Short Chain Fatty Acids to Treat Selected Lymphomas

Since the present example is an idea based upon the properties of SCFAs, combined with the difficulties achieving long term remission and preventing relapse of selected lymphomas, it can be useful to test this approach in 1-2 preclinical models for each selected lymphoma to establish proof-of-principle for human trials. The invention itself simply involves oral administration of SCFAs at the time of diagnosis either alone or in combination with standard of care therapy. Moreover, in mouse models, treatment prior to the development of lymphoma can establish whether SCFAs can delay or block tumor development. Given that these cancers in people are often accompanied by multiple genetic aberrations that may be present prior to the clinical phase of the disease, and that some of these tumors may have associated hereditary predisposition, suggest that SCFAs may (at a minimum) help to prevent recurrence/relapse.

SCFAs could be used (1) alone or in combination with standard of care treatments for selected lymphomas that depend upon constitutive activation of NF-κB, since the SCFAs used herein block NF-κB activity, (2) to delay or prevent lymphoma recurrence/relapse, (3) to decrease the toxicity profiles of standard of care treatments, thereby increasing long term quality of life, (4) to possibly intervene in high risk patients prior to the appearance of lymphoma, and (5) to target lymphomas by virtue of SCFAs histone deacetylase (HDAC) inhibitory activity, which is not part of any other therapeutic approach in practice or in development. These features will help to extend the invention to better treat patients with high tumor loads.

Suggested Treatment:

The daily oral dose is 4-5 g of butyrate in enteric coated, extended release capsules, 3 times/day continuously.

Treatment with butyrate could be done in combination with reduced doses of steroids and chemodrugs.

Example 8: Use of Short Chain Fatty Acids to Treat Leukemias

Philadelphia chromosome negative (Ph−) myeloproliferative neoplasms (MPNs) include polycythemia vera (PV), essential thrombocytosis (ET), and myelofibrosis (MF), all of which may evolve into acute myeloid leukemia (AML). MPNs are characterized by constitutive activation of the myeloproliferative leukemia (MPL) oncogene and the signaling molecule, JAK2 (usually by mutation). STAT-1, -3 and -5, MAPK, ERK and AKT/PI3K, all support cytokine independent growth in PV, ET and MF. The tumor suppressor and epigenetic modifier, ten-eleven translocation 2 (TET2) is also frequently mutated in these cells, suggesting that activation of JAK2 and inactivation of TET2 are drivers of AML. They block differentiation and promote self-renewal. Ph-MPNs are relatively rare, ranging from 90-120 cases per 100,000. A variety of tyrosine kinase inhibitors (TKIs) have been developed to block JAK/STAT hyperactivation, but this is not curative in many patients and is associated with significant toxicity.

Butyrate has been shown to block nuclear translocation of STAT1, which blocks JAK2 activation. Further, butyrate and propionate are HDAC inhibitors. Elevated HDAC activity inhibits retinoic acid (RA) induced differentiation, so it is expected that butyrate/propionate+retinoic acid may prevent the progression and/or relapse of MPNs.

Pediatric ALL is also characterized by constitutive activation of the JAK/STAT pathway, which is inhibited by butyrate. In addition, butyrate activates p53, which is otherwise down-regulated in ALL. Further, the SCFA valproate inhibits TGFbeta1 and PI3K signaling in ALL, all of which suggest that SCFA intervention would demonstrate efficacy in this context. This is especially important in pediatric and adult ALL, since minimal residual disease is common after initial chemotherapy and relapse time is characteristically short.

Since the present example is based upon the properties of SCFAs, combined with the difficulties achieving long term remission and preventing relapse of AML and other leukemias, it would be useful to test this approach in 1-2 pre-clinical models for each selected leukemia to establish proof-of-principle for human trials. The invention itself includes oral administration of one or more SCFA therapeutic compounds at the time of diagnosis, either alone or in combination with standard of care therapy. Moreover, in mouse models, treatment initiated at the time of diagnosis will establish whether SCFAs can delay or block tumor progression. Given that these cancers in people are often accompanied by multiple genetic aberrations that may be present prior to the clinical phase of the disease, and that some of these tumors may have associated hereditary predisposition, suggest that SCFAs may (at a minimum) help to prevent recurrence/relapse.

Experiments include introducing AML or ALL cell lines (or banked primary cells from patients with the same disease) into immunodeficient mice (NOD/SCID) followed by SCFA treatment or placebo for different periods of time. Periodic blood samples will be analyzed for minimal residual disease by PCR amplification of the genetic rearrangements that are common in AML or ALL in clinical samples or known to be associated with a particular cell line that was used for injection. If commercially available transgenic mice carrying the major genetic lesions characteristic of AML or ALL are commercially available, then experiments could be planned to test whether SCFAs could alter disease pathogenesis.

SCFAs could be used (1) alone or in combination with standard of care treatments for selected leukemias (AML and ALL) that depend upon constitutive activation of JAK/STAT, since the SCFAs used herein block JAK/STAT activity, (2) to delay or prevent leukemia recurrence/relapse, (3) to decrease the toxicity profiles of standard of care treatments started at the time of diagnosis, thereby increasing long term quality of life. These features will help to extend the invention to better treat patients with high tumor loads.

Currently, treatment includes two phases. The first phase, referred to as induction, often includes chemotherapy with ara-C and daunomycin, which lowers the white blood cell count and destroys the bone marrow. Sometimes a third drug, cladribine (Leustatin, 2-CdA), is given as well. Induction is considered successful if remission is achieved. However, induction leaves patients susceptible to fatal infections for up to several weeks, and during that time, they remain hospitalized. The second phase, referred to as consolidation, which includes long term high dose ara-C. Alternatively, allogeneic or autologous stem cell transplant could be considered, although consolidation is associated with increased risk of death.

Constitutively activated HDAC has been observed in many types of leukemias, and so synthetic HDAC inhibitors have been proposed as interventional strategies. However, none have entered human clinical trials, although valproate and phenylbutyrate are under evaluation for selected lymphomas. In acute promyelocytic leukemia (APL), a variant of AML, inhibition of HDAC1/2 promotes differentiation and apoptosis. However, treatment of preleukemic cells with the same HDAC inhibitors promote cell proliferation, suggesting that SCFAs may be of use to block tumor relapse, but may not prevent tumor onset. The potential advantage of using the mixture of SCFAs including butyrate and propionate for AML relapse is that they will be efficacious without appreciable side effects. Since SCFA associated HDAC inhibitory activity is reversible, the present example provides a potentially sound way of balancing efficacy while lowering the risk of toxic or other adverse effects common in other therapeutic approaches. This may be especially true in the context of dealing with tumor recurrence/relapse where combination therapies may turn out to be the best option.

Suggested Treatment:

The daily oral dose is 4-5 g of butyrate in enteric coated, extended release capsules, 3 times/day continuously.

Treatment with butyrate could be done in combination with reduced doses of steroids and chemodrugs.

Example 9: Use of Short Chain Fatty Acids in Treatment or Prevention of Adverse Effects Associated with CAR-T Therapy The probability of the present example working in pre-clinical models is high given the goal of cancer immunotherapy and the known immunomodulatory functions of SCFAs. SCFAs can be taken orally, are non-toxic, and have no problem crossing both the gut epithelium and blood-brain barrier, which are combined advantages not available by other approaches. Since immune-modulation by SCFAs is reversible, the present example provides a sound way of balancing efficacy while lowering the risk of adverse effects for CAR-T and other cancer immunotherapeutic approaches.

For example, in one aspect, the invention provides an adjunct therapy to (1) ameliorate a cytokine storm seen in some patients given CAR-T, (2) provide neuroprotection for patients experiencing these adverse effects, (3) immune-modulate CAR-T cell activity without using cytotoxic chemotherapy or systemic corticosteroids, (4) also have anti-tumor properties by virtue of SCFAs histone deacetylase (HDAC) inhibitory activity in both liquid and solid tumors where the Warburg effect shunts SCFAs to the nucleus, and (5) SCFAs are broadly anti-inflammatory because they modulate NF-κB, which directly stimulates production of IL-6, TNFα, and IFNγ, all of which are commonly elevated in a cytokine release syndrome (CRS). SCFAs also down-regulate the production of TNFα and IL-6 from macrophages, thereby potentially ameliorating macrophage activation syndrome, which is also a documented adverse effect of CAR-T therapy. This will help to extend the invention to better treat patients with high tumor loads.

Two CD-19 targeted CAR-T therapies are approved by FDA for the treatment of children with acute lymphoblastic leukemia and for adults with advanced lymphomas.

Cytokine Release Storm (CRS) is considered to be an "on-target' side effect, meaning T-cells are active. However, it can lead to dangerously high fever and quick drop in blood pressure. Patients experiencing severe CRS all had particularly high levels of cytokine IL-6 (secreted by T cells and macrophages in response to inflammation). Tocilizumab (which blocks IL-6 activity) become a standard therapy for managing CRS. The approach worked, resolving the problem in most patients. However, patients treated with Tocilizumab are at very high risk for developing serious infections that may lead to hospitalization or death.

Butyrate (Yuan H, Liddle F J, Mahajan S, Frank D A. IL-6-induced survival of colorectal carcinoma cells is inhibited by butyrate through down-regulation of the IL-6 receptor. Carcinogenesis. 2004; 25(11):2247-55) and propionate (Nastasi C, Fredholm S, Willerslev-Olsen A, et al. Butyrate and propionate inhibit antigen-specific CD8(+) T cell activation by suppressing IL-12 production by antigen-presenting cells. Sci Rep. 2017; 7(1):14516) were shown to inhibit IL-6, thus can be considered as a co-treatment option.

SCFAs should be given in parallel to chemotherapy: several days before CAR-T cell infusion (only SCFAs), and up to several weeks after CAR-T cell infusion (SCFAs in combination with significantly reduced doses of chemodrug(s)). The daily oral dose is 5-6 g of butyrate and 2-3 g of propionate in enteric coated, extended release capsules, 3 times/day.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of causing disappearance of a psoriatic lesion in a subject in need thereof, comprising administering to the subject a therapeutically effective amount of a pharmaceutical composition, wherein the pharmaceutical composition comprises in a unit dosage form:
    a) a therapeutically-effective amount of butyric acid or a pharmaceutically-acceptable salt thereof;
    b) a therapeutically-effective amount of propionic acid or a pharmaceutically-acceptable salt thereof;
    c) a therapeutically-effective amount of an inorganic magnesium salt; and
    d) a therapeutically-effective amount of Vitamin D3,
wherein the unit dosage form does not comprise a fatty acid that has at least five carbon atoms, and wherein the disappearance of the psoriatic lesion occurs within about three weeks of administration of the unit dosage form to the subject.

2. The method of claim 1, wherein the administering is oral.

3. The method of claim 1, wherein the therapeutically-effective amount of butyric acid or the pharmaceutically-acceptable salt thereof is about 800 mg.

4. The method of claim 1, wherein the therapeutically-effective amount of propionic acid or the pharmaceutically-acceptable salt thereof is about 50 mg.

5. The method of claim 1, wherein the therapeutically-effective amount of the inorganic magnesium salt is about 10 mg.

6. The method of claim 1, wherein the therapeutically-effective amount of Vitamin D3 is about 50 IU.

7. The method of claim 1, wherein the administering is three times a day for at least one week.

8. The method of claim 1, wherein the administering is three times a day for at least one week, wherein the administering is oral, wherein the therapeutically-effective amount of butyric acid or the pharmaceutically-acceptable salt thereof is about 800 mg, wherein the therapeutically-effective amount of propionic acid or the pharmaceutically acceptable salt thereof is about 50 mg, wherein the therapeutically-effective amount of the inorganic magnesium salt is about 10 mg, and wherein the therapeutically-effective amount of Vitamin D3 is about 50 IU.

9. A method of causing disappearance of a psoriatic lesion in a subject in need thereof, comprising administering to the subject a therapeutically effective amount of a pharmaceutical composition, wherein the pharmaceutical composition comprises in a unit dosage form, a combination of fatty acids, wherein the combination of fatty acids consists of about 800 mg butyric acid or a pharmaceutically-acceptable salt thereof; and about 50 mg propionic acid or a pharmaceutically-acceptable salt thereof, wherein the disappearance of the psoriatic lesion occurs within about 3 weeks of administration to the subject of the unit dosage form.

10. The method of claim 9, wherein the unit dosage form further comprises a therapeutically-effective amount of an inorganic magnesium salt.

11. The method of claim 10, wherein the therapeutically-effective amount of the inorganic magnesium salt is about 10 mg.

12. The method of claim 9, wherein the unit dosage form further comprises a therapeutically-effective amount of Vitamin D3.

13. The method of claim 12, wherein the therapeutically-effective amount of Vitamin D3 is about 50 IU.

14. The method of claim 9, wherein the administering is oral.

15. The method of claim 9, wherein the administering is three times a day for at least one week.

* * * * *